US010632324B2

(12) United States Patent
Barolet

(10) Patent No.: US 10,632,324 B2
(45) Date of Patent: Apr. 28, 2020

(54) METHOD FOR THE TREATMENT OF SKIN TISSUES

(71) Applicant: 9127-4910 Quebec Inc., Laval (CA)

(72) Inventor: Daniel Barolet, Rosemere (CA)

(73) Assignee: 9127-4910 QUEBEC INC., Laval (CA)

( * ) Notice: Subject to any disclaimer, the term of this patent is extended or adjusted under 35 U.S.C. 154(b) by 208 days.

(21) Appl. No.: 15/964,552

(22) Filed: Apr. 27, 2018

(65) Prior Publication Data
US 2018/0311507 A1   Nov. 1, 2018

Related U.S. Application Data

(60) Provisional application No. 62/490,982, filed on Apr. 27, 2017.

(51) Int. Cl.
*A61N 5/06*     (2006.01)
*A61B 18/20*    (2006.01)
*A61B 18/00*    (2006.01)

(52) U.S. Cl.
CPC .......... *A61N 5/0616* (2013.01); *A61B 18/203* (2013.01); *A61N 5/062* (2013.01); *A61B 2018/00476* (2013.01); *A61N 5/0625* (2013.01); *A61N 2005/0651* (2013.01); *A61N 2005/0652* (2013.01); *A61N 2005/0659* (2013.01); *A61N 2005/0663* (2013.01)

(58) Field of Classification Search
CPC ...... A61N 5/06; A61N 5/0613; A61N 5/0616; A61N 5/062; A61N 5/0625; A61N 2005/0626–0629; A61N 2005/065; A61N 2005/0651; A61N 2005/0658; A61N 2005/0659
See application file for complete search history.

(56) References Cited

U.S. PATENT DOCUMENTS

| 5,632,739 | A  | 5/1997  | Anderson et al. |
| 5,643,334 | A  | 7/1997  | Eckhouse et al. |
| 5,814,008 | A  | 9/1998  | Chen et al.     |
| 5,851,181 | A  | 12/1998 | Talmor          |
| 5,871,479 | A  | 2/1999  | Furumoto et al. |
| 5,913,884 | A  | 6/1999  | Trauner et al.  |
| 6,022,455 | A  | 2/2000  | Otake           |
| 6,156,030 | A  | 12/2000 | Neev            |
| 6,387,089 | B1 | 5/2002  | Kreindel et al. |
| 6,547,781 | B1 | 4/2003  | Furumoto        |
| 6,595,985 | B1 | 7/2003  | Tobinick        |
| 6,626,932 | B2 | 9/2003  | Whitehurst      |
| 6,746,444 | B2 | 6/2004  | Key             |
| 6,878,144 | B2 | 4/2005  | Altshuler et al.|
| 6,887,260 | B1 | 5/2005  | McDaniel        |

(Continued)

OTHER PUBLICATIONS

Augustin C. Barolet, Gregory Cormack, Daniel Barolet M.D., "5-ALA photopreparation using pulsed NIR enhances skin fluorescence via temperature-independent cell signaling pathways," Proc. SPIE 10477, Mechanisms of Photobiomodulation Therapy XIII, 104770K (Feb. 8, 2018); https://doi.org/10.1117/12.2290507.*

(Continued)

*Primary Examiner* — Eugene T Wu

(57) ABSTRACT

A method for treating skin tissues including irradiating the skin tissues with infrared light between about 16 and about 72 hours prior to photodynamic therapy.

31 Claims, 33 Drawing Sheets

(56) References Cited

U.S. PATENT DOCUMENTS

| | | |
|---|---|---|
| 6,902,563 B2 | 6/2005 | Wilkens et al. |
| 7,198,634 B2 | 4/2007 | Harth et al. |
| 7,914,523 B2 | 3/2011 | Barolet et al. |
| 8,226,634 B2 | 7/2012 | Barolet |
| 9,737,728 B2 | 8/2017 | Barolet |
| 2002/0095143 A1 | 7/2002 | Key |
| 2002/0123782 A1 | 9/2002 | Sierra |
| 2002/0128695 A1 | 9/2002 | Harth |
| 2003/0004556 A1 | 1/2003 | Mcdaniel |
| 2003/0130649 A1 | 7/2003 | Murray |
| 2003/0208245 A1 | 11/2003 | Mahadevan-Jansen |
| 2003/0212127 A1 | 11/2003 | Glassman et al. |
| 2004/0034341 A1 | 2/2004 | Altshuler et al. |
| 2004/0073277 A1 | 4/2004 | Geronemus |
| 2004/0127815 A1 | 7/2004 | Marchitto et al. |
| 2004/0162596 A1 | 8/2004 | Altshuler et al. |
| 2004/0167501 A1 | 8/2004 | Island |
| 2005/0045189 A1 | 3/2005 | Jay |
| 2005/0143792 A1 | 6/2005 | Jay |
| 2005/0197681 A1 | 9/2005 | Barolet et al. |
| 2006/0004347 A1 | 1/2006 | Altshuler et al. |
| 2006/0074468 A1 | 4/2006 | Neev |
| 2006/0212025 A1 | 9/2006 | McDaniel |
| 2006/0269580 A1* | 11/2006 | Cole ............... A61N 5/0616 424/401 |
| 2007/0231255 A1 | 10/2007 | Barolet et al. |
| 2007/0255359 A1 | 11/2007 | Neev |
| 2008/0188558 A1 | 8/2008 | Godal |
| 2009/0022799 A1 | 1/2009 | Barman |
| 2009/0112192 A1* | 4/2009 | Barolet ............ A61N 5/0616 606/9 |
| 2009/0131499 A1 | 5/2009 | Castro et al. |
| 2009/0247932 A1* | 10/2009 | Barolet ............ A61N 5/0616 604/20 |
| 2010/0137439 A1 | 6/2010 | Wulf |
| 2011/0224598 A1* | 9/2011 | Barolet ............ A61M 37/00 604/20 |
| 2012/0010603 A1 | 1/2012 | Milner et al. |
| 2013/0274834 A1* | 10/2013 | Barolet ............ A61N 5/062 607/88 |

OTHER PUBLICATIONS

Daniel Barolet, Light-Emitting Diodes (LEDs) in Dermatology, Dec. 4, 2008, Seminars in Cutaneous Medicine and Surgery, vol. 27, pp. 227-238.

* cited by examiner

Upper Middle Back
Primos 3-D Microtopography

METHOD FOR THE TREATMENT OF SKIN TISSUES

FIELD OF THE INVENTION

The present invention relates to the treatment of skin tissues. Specifically, the present invention is concerned with a method for the treatment of skin tissues including irradiating the skin tissues with infrared radiation.

BACKGROUND OF THE INVENTION

An important role of skin is to provide protection against infection and physical damage. However, skin also prevents many substances from crossing its epidermal barrier. The skin is not a natural gateway that transdermal delivery systems can exploit; while oral or pulmonary delivery might take place in the gut or lungs, the skin is a physical barrier to overcome.

The skin's ability to inhibit/control the movement of substances across its surface implies that only a small proportion of pharmaceutically active compounds, for example, are suitable for conventional transdermal delivery. Many compounds will be absorbed by the skin; however the absorption typically involves relatively small quantities/concentrations of external molecules per area of skin, per hour, requiring that unpractical large skin contact areas be used to achieve therapeutically effective concentrations of substances via transcutaneous delivery. Furthermore, many compounds do not penetrate the skin at all.

Transcutaneous delivery remains to these days a challenging route of drug administration. A typical challenge faced with inhalable or oral delivery is drug concentration, as it regards the delivery of sufficient quantities of the drug to relatively inaccessible inner surfaces (internal organs) where the delivered compound crosses into the blood. For instance, for systemic delivery, inhalers and formulations for inhalation must incorporate advanced designs to allow deposition into the lungs. Oral technologies must protect the drug from the harsh environment in the stomach for it to reach the epithelium intact. In contrast, while transcutaneous formulations can be applied directly to the surface, the medication is intended to cross the skin. The dense capillary bed close beneath the surface suggests easy access to the systemic circulation; however the compound must cross the skin barrier.

Potential benefits of transcutaneous delivery have spurred several scientists to overcome challenges faced by skin as a barrier by developing active transdermal delivery technologies. These systems use energy to enhance the extent and rate at which pharmaceutical compounds cross the 10 to 20 micrometers dead layer of the skin, the stratum corneum.

Technologies currently under development can be mostly divided into two broad categories. The first category rests on iontophoresis, the ability of an electric current to cause charged particles to move. A pair of adjacent electrodes, placed on the skin, sets up an electrical potential between the skin and the capillaries below. At the positive electrode, positively charged drug molecules are driven away from the skin's surface toward the capillaries. Conversely, negatively charged drug molecules would be forced through the skin at the negative electrode. However, this method requires that the molecules used be charged, which is not automatically the case for all substances of interest. It is also relatively difficult to deliver relatively large molecules using this approach. Finally, this method implies that electrodes and drug formula be set in contact with the skin which can sometimes involve a long contact time for optimized drug delivery, depending on expected rate delivery, if any.

The other category of active transdermal delivery is known as poration. It involves high-frequency pulses of energy, in a variety of forms (radiofrequency (RF) electrical current, lasers, heat, and ultrasound) temporarily applied to the skin to disrupt the stratum corneum, the layer of skin that stops many drug molecules crossing into the bloodstream. Unlike iontophoresis, the energy used in poration technologies is not used to transport the drug across the skin, but to facilitate/allow its movement/penetration. Poration provides a "window" through which drug substances can pass much more readily and rapidly than they would normally. Although this method may be useful to allow some drug molecules to reach dermal capillaries, there is no evidence that it would promote preferential absorption and deposition to specific target structures within the dermis.

For example, the Israeli company, TransPharma Medical, is using alternating current at radio frequencies to create aquatic throughways, about 100 micrometers wide, across the stratum corneum. The number of active electrodes determines the number of pores and thus, amongst other factors, the rate at which drug will cross the skin. Importantly, newly created channels only reach as far as the epidermis, where there are no nerves or blood vessels. The main limitation of this technology is the depth of penetration of these channels within the epidermis so that not enough drug molecules are able to get to targeted structures in the dermis to achieve a significant clinical improvement.

Laser Light

Norwood Abbey's Laser Assisted Delivery® (LAD) technology comprises an electronic, handheld Er:YAG laser device, which is pressed against the skin exposing the treatment area to a burst of low level laser light. Although this process disrupts the barrier function of the skin long enough to allow drug molecules to move through more quickly, the physiological effects triggered by the laser are relatively mild, involving rearrangement of lipids and proteins or removal of dead cells. This method, which can involve skin contact, has therefore the potential of allowing only limited movements across the epidermal layer.

U.S. Pat. No. 5,814,008, issued Sep. 29, 1998 to Chen et al., discloses a method of photodynamic therapy (PDT) wherein the treated tissue may be heated before the application of a photosensitizer, to facilitate its perfusion into the tissue and enhance efficacy of the subsequent light therapy. The heating may be achieved by a number of means, preferably by irradiating the tissue with a light having a wavelength substantially different than the wavelength of light used for the PDT treatment. However, the PDT treatment disclosed in this document is invasive in nature and no transcutaneaous delivery of the photosensitizer is therefore contemplated as the radiation is applied through a probe inserted within the tissues to be treated.

Heat

To ablate the stratum corneum, bursts of electric current cause points of filaments in contact with the skin to heat up for a few milliseconds at a time. Behind these filaments is the drug reservoir, for example a patch, from which the formulation diffuses past the filament and through the skin. The need for repeated microtrauma to the skin, the requirement of sometimes large contact areas to achieve proper drug concentration and the need for a patch with prolonged contact time are all disadvantages of this method. Also, almost perfect contact of the heating apparatus (pad, etc.) must be ensured during the procedure to provide a uniform preparation of the targeted area.

Sound

The final energy form, sound (or more specifically, ultrasound) is also being used for transdermal delivery. Sound technology, known as SonoPreparation®, uses a 15-second burst of ultrasound at 55 kHz. Sound waves create cavitations bubbles in the tissue, disrupting the lipid bilayers of stratum corneum cells, which results in the creation of microchannels. The SonoPreparation device consists of a handpiece, linked by a wire to a base unit, pressing an ultrasonic horn onto the skin treatment area. The limitations of this method are the same as for the ones described previously for heat.

In view of the above, there is a need to provide novel methods for the treatment of skin tissues.

SUMMARY OF THE INVENTION

In a first broad aspect, the invention provides a method for treating skin tissues, the skin tissues defining an epidermal layer and a sub-epidermal layer, the epidermal layer defining a skin surface and the sub-epidermal layer extending from the epidermal layer substantially opposite to the skin surface, the method comprising:

positioning a radiation source outside of the skin tissues at a predetermined distance from the skin surface;

powering the radiation source so as to produce infrared radiation having a predetermined spectrum and a predetermined power;

irradiating the sub-epidermal layer with the infrared radiation through the epidermal layer, the predetermined spectrum and the predetermined power being such that the infrared radiation is absorbed to a larger degree in the sub-epidermal layer than in the epidermal layer In some embodiments of the invention, the predetermined spectrum includes wavelengths contained within an interval of from about 750 nm to about 1200 nm, or in an interval of from about 800 nm to about 1000 nm. In very specific embodiments of the invention, the predetermined spectrum includes wavelengths contained within the group consisting of 870 nm and 970 nm.

In some embodiments of the invention, the predetermined spectrum has a bandwidth of about 30 nm or less. For example, this may be achieved when positioning the radiation source includes positioning a Light Emitting Diode (LED) outside of the skin tissues at the predetermined distance from the skin surface.

In some embodiments of the invention, the predetermined power and the predetermined distance are such that an intensity of the infrared radiation at the skin surface is from about 1 mW/cm$^2$ to about 1 W/cm$^2$, or, in other embodiments, from about 30 mW/cm$^2$ to about 250 mW/cm$^2$.

In some embodiments of the invention, irradiating the sub-epidermal layer is performed for a predetermined duration, the predetermined duration being of from about 1 minute to about 1 hour, the method further comprising stopping the irradiation of the sub-epidermal layer after the predetermined duration. The embodiments may be performed using the above-mentioned predetermined spectrums and intensities of the infrared radiation at the skin surface In some embodiments of the invention, the method includes measuring a skin temperature of the skin tissues while irradiating the sub-epidermal layer with the infrared radiation; and stopping the irradiation of the sub-epidermal layer when the skin temperature reaches a predetermined temperature. For example, the predetermined temperature is from about 38 C to about 41 C, and in specific embodiments of the invention, about 41 C.

In a variant, the method includes applying a treatment substance on the skin surface. For example, the treatment substance is applied after irradiating the sub-epidermal layer with the infrared radiation. In some embodiments, the treatment substance includes a photo-activatable substance, the method further comprising irradiating the skin tissues with radiation having a spectrum and a power density suitable for activating the photo-activatable substance. Examples of suitable treatment substances include porphyrin, chlorine, xanthene, and phtalocyanine derivatives. These substances are usable to treat many skin conditions, such as for example actinic karatosis, acne, inflammatory acne, diffuse sebaceous glands hyperplasia, other sebaceous gland disorders, neoplastic disorders, other actinic damages, collagen-related skin diseases (connective tissue disorders), other sweat gland disorders, chronic and acute inflammation, psoriasis, granulomatous skin conditions, vascular lesions, benign pigmented lesions, hair disorders and some skin infections.

The method is performable in vivo, for example on a human subject. However, in alternative embodiments of the invention, the method is also performable on non-human subjects and in vitro.

In some embodiments, the method is performed such that irradiating the sub-epidermal layer with the infrared radiation is performed in a manner such that the skin surface is irradiated substantially uniformly over a treatment area. For example, the intensity of the radiation on the skin surface varies by less than about 15% over the treatment area.

In some embodiments of the invention, the skin tissues include pores, irradiating the sub-epidermal layer with the infrared radiation being performed in a manner such that the infrared radiation causes the pore to increase in diameter.

In some embodiments of the invention, irradiating the sub-epidermal layer with the infrared radiation is performed for a predetermined duration, the predetermined power, the predetermined distance and the predetermined duration being such that the skin is irradiated with a fluence of from about 50 J/cm$^2$ to about 300 J/cm$^2$.

For the purpose of the present description, the term sub-epidermal refers to skin layers located under the epidermis and includes both the dermis and the hypodermis. However, the proposed method may have an effect on only one or on both of these layers without departing from the scope of the present invention.

IR exposure as described herein is a new way to deliver, for example through a substantially uniform penetration, a given compound in the skin. The opening of pores takes place without mechanical manipulation or alteration of skin integrity. The nature of the substance or compound might have less influence over this delivery procedure as this invention refers to the induction of a physiological process: heat generated pore dilatation and physicochemical permeation (to pass through epidermal openings or interstices) secondary to photobiochemical vibrational alterations. As oppose to existing mechanical (microdermabrasion) or purely chemical (acetone scrub) pre-PDT skin preparations, the present method uses non-ablative IR photons non-invasively to achieve inside-out thermal benefits without any damage to skin. A further benefit of this invention over existing technologies is the development of a well controlled, users friendly, and consistent procedure, easy to use in a clinical setting.

The radiant IR skin preparation method provides numerous advantages. The inside-out heat transfer mechanism proper to this method does not imply skin contact with a light source, providing uniformity in the preparation of the entire treatment area. Moreover, this method, while triggering a physiological reaction at the treatment site, is independent of the molecule size and drug rate for transcutaneous delivery. And as this skin preparation method occurs prior to any drug application, it cannot alter the drug integrity in any mean. Finally, IR radiant skin preparation can be performed from up to an hour before treatment in order to open skin pore for optimal drug delivery, according to selected irradiation parameters.

This innovative method provides of relatively quick and easy way to enhance drug absorption as IR exposure tries to reproduce the human body normal physiological reactions for heat dissipation, leading to the opening of skin pores.

The challenge of selecting the right optimal light source parameters for successful PDT remains underestimated. When compared to high energy enablers such as lasers or IPLs, high end LED devices are better able to meet the challenge and can be used as the light source of choice for enhanced PDT. This presentation covers the fundamentals of an improved procedure for effective PDT applications.

First, the use of an LED source avoids, or at least reduces, thermal peak effect on the photosensitizer—so called thermal effects—usually encountered with thermal technologies such as IPLs and lasers (i.e. PDL; Pulsed Dye Lasers). LED technology clearly allows for progressive photoactivation of photosensitizers. Furthermore, dose-rate is increasingly believed to be one of the important criteria as opposed to total dose (fluence). Uniformity must also be addressed as a high power LED light source covering large treatment areas must reduce irregular cold and hot spots. A high power non-thermal device offers the threshold energy level required for effective careful activation of the photosensitizer with minimal side effects. In addition, the wavelength specification is key to matching selective absorption peaks of the photosensitizer—a wavelength with a narrow spectral band reaching deeper dermal structures should be used in many instances. In fact, the use of a dual wavelength (red and blue) LED light source enhances PDT results for acne and other sebaceous disorders. Red wavelength (630 nm) can reach the sebaceous glands and blue (405 nm) photobleaches any residual protoporphyrin IX (PpIX) in the epidermis, thereby also reducing post-treatment photosensitivity. Indeed, a dual-wavelength LED device optimizes PDT results by providing a superior activation of the photosensitizer—deep at the target structure—for maximized clinical effect and fewer side effects.

Another challenge rests in reaching deeper in the skin, where the sebaceous glands are, for enhanced clinical effect in the dermis, while triggering fewer side effects on the epidermis. The entire photon delivery method, prior and during PDT, could hold part of the answer for more effective treatments. Not only can LED sources be used to stimulate a photosensitizer but high power infrared LEDs can prepare the skin prior to treatment. A new pre-PDT method has been successfully used to presumably increase in situ conversion of 5-ALA to PpIX due to slight temperature elevation induced by radiant IR exposure.

Limitations for PDT experimentation and optimization are linked to the availability of photosensitizers. While there are currently only two clinically approved photosensitizers: Levulan™ and Metvix™, promising agents are in the industry pipeline. Moreover, their significant cost does temper widespread use of PDT and explains the poor-ROI of some companies' independent studies.

In another broad aspect, there is provided a method for treating skin tissues, said skin tissues defining an epidermal layer and a sub-epidermal layer, said epidermal layer defining a skin surface and said sub-epidermal layer extending from said epidermal layer substantially opposite to said skin surface, said method comprising: positioning a radiation source outside of said skin tissues at a predetermined distance from said skin surface, said radiation source including light emitting diodes; powering said light emitting diodes so as to produce infrared radiation having a predetermined spectrum and a predetermined power; irradiating a predetermined region of said sub-epidermal layer for a predetermined duration of from 1 minute to 1 hour with said infrared radiation through said epidermal layer, said predetermined spectrum and said predetermined power being such that said infrared radiation is absorbed to a larger degree in said sub-epidermal layer than in said epidermal layer; waiting for a predetermined delay after irradiating said predetermined region for said predetermined duration; and applying a treatment substance on said skin surface immediately after said predetermined delay.

For example, said predetermined delay is between 24 and 72 hours. In another example, said predetermined delay is about 48 hours. In another example, said predetermined delay is between 36 and 60 hours.

In some embodiments, said predetermined spectrum includes wavelengths contained within an interval of from about 800 nm to about 1000 nm.

In some embodiments, said predetermined spectrum includes a peak at about 940 nm, said peak having a bandwidth of less than about 30 nm.

In some embodiments, predetermined spectrum includes a peak at about 870 nm, said peak having a bandwidth of less than about 30 nm.

In some embodiments, predetermined spectrum includes a peak at about 970 nm, said peak having a bandwidth of less than about 30 nm.

In some embodiments, said method further comprises: measuring a skin temperature of said skin tissues while irradiating said sub-epidermal layer with said infrared radiation; and stopping irradiation of said sub-epidermal layer when said skin temperature reaches a predetermined temperature.

In some embodiments, said predetermined temperature is about 38 C.

In some embodiments, said predetermined temperature is about 41 C.

In some embodiments, said sub-epidermal layer is irradiated with a fluence of from about 50 $J/cm^2$ to about 300 $J/cm^2$.

In some embodiments, said sub-epidermal layer is irradiated with a fluence of from about 50 $J/cm^2$ to about 300 $J/cm^2$ with light having a wavelength selected from the group consisting of 870 nm, 940 nm and 970 nm and a bandwidth of less than about 30 nm, under conditions such that said skin tissues remain at a temperature smaller than about 41 C.

In some embodiments, said treatment substance includes a photo-activatable substance, said method further comprising irradiating said skin tissues with radiation having a spectrum and a power density suitable for activating said photo-activatable substance.

In some embodiments, said treatment substance is selected from the group consisting of porphyrin, chlorine, 5-ALA, xanthene and phtalocyanine derivatives.

In some embodiments, said skin tissues include skin tissues having a condition selected from the set consisting of actinic karatosis, acne, inflammatory acne and diffuse sebaceous glands hyperplasia.

In some embodiments, said skin tissues include skin tissues having a skin condition selected from the set consisting of sebaceous gland disorders, neoplastic disorders, actinic damage, collagen-related skin diseases, connective tissue disorders, sweat gland disorders, chronic and acute inflammation, psoriasis, granulomatous skin conditions, vascular lesions, benign pigmented lesions, hair disorders and skin infections.

In some embodiments, said method is performed in vivo.

In some embodiments, said method is performed on a human subject.

In some embodiments, said skin tissues include pores, irradiating said sub-epidermal layer with said infrared radiation being performed in a manner such that said infrared radiation causes said pore to increase in diameter.

In some embodiments, said pulsed radiation has a duty cycle of between 15% and 85%.

In some embodiments, said pulsed radiation has a duty cycle of about 50%.

In some embodiments, said predetermined delay is between 8 hours and 72 hours.

In some embodiments, said predetermined delay is at least 24 hours.

In some embodiments, said infrared radiation has a power of from about 1 mW/cm$^2$ to about 1 W/cm$^2$.

In some embodiments, said infrared radiation has a power of from about 30 mW/cm2 to about 250 mW/cm2.

In some embodiments, said infrared radiation has a power of from about 20 mW/cm2 to about 100 mW/cm2.

In some embodiments, said radiation includes only said infrared radiation.

In some embodiments, said infrared radiation includes pulses of a pulse duration separated by an inter-pulse interval.

In some embodiments, said pulse duration is from about 100 microseconds to about 5 milliseconds.

In some embodiments, said pulse duration is from about 250 microseconds to about 1 millisecond.

In some embodiments, said pulse duration is about 500 microseconds.

In some embodiments, said inter-pulse interval is from about 50 microseconds to about 0.5 millisecond.

In some embodiments, said inter-pulse interval is from about 50 microseconds to about 0.5 millisecond.

In some embodiments, the pulses are grouped in pulse trains, all pulses within a pulse train having the same pulse duration and being separated from each other by the same inter-pulse interval, the pulse trains being separated from each other by an inter-pulse train interval larger than the inter-pulse interval.

In some embodiments, the inter-pulse train interval is from about 500 microsecond to about 1 second.

In some embodiments, the inter-pulse train interval is from about 750 microseconds to about 500 milliseconds.

In some embodiments, the inter-pulse train interval is from about 500 microseconds to about 2.25 milliseconds.

In some embodiments, a number of pulses within each pulse train is from 2 to 1000 pulses In some embodiments, a number of pulses within each pulse train is from 3 to 10 pulses.

The present application incorporates by reference in its entirety U.S. Provisional Patent Application 62/490,982 filed Apr. 27, 2017.

Other objects, advantages and features of the present invention will become more apparent upon reading of the following non restrictive description of preferred embodiments thereof, given by way of example only with reference to the accompanying drawings.

DESCRIPTION

While the experiments described herein concern heating the skin of humans and the absorption of photosensitive substances in humans, one of ordinary skilled in the art will readily appreciate that these experiments may be predictive of other biological effects in humans or other mammals and/or may serve as models for use of the present invention in humans or other mammals, whether in vitro or in vivo.

In the present document, the terminology "about" designates variations from nominal values that do not materially affect the results of the claimed method. For examples, "about" is present to accommodate variations due to experimental uncertainties or to variations that are so close to these nominal values that the results of the claimed method is the same, within measurement errors, whether the nominal value of a value covered by "about" is used.

To increase temperature, heat may be transmitted to skin tissues by conduction through a direct contact, by convection when heat is conveyed by a warm medium such as air or water and by radiant energy when heat is given off from a heated body following IR irradiation.

Figure 1A:
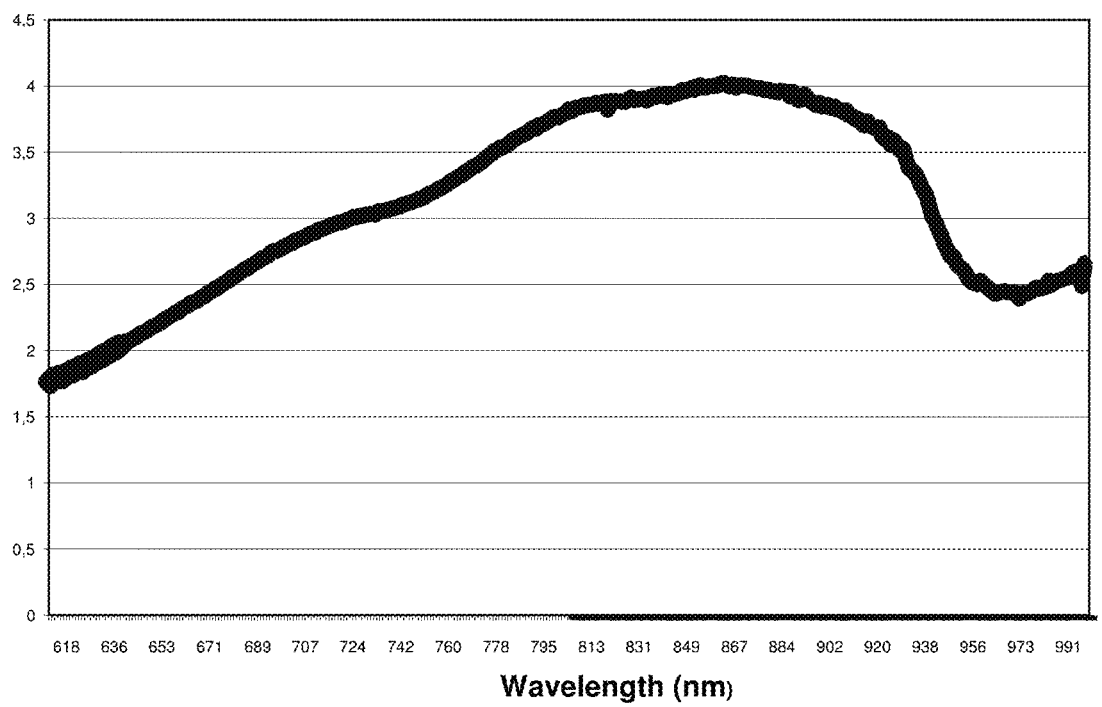
FIG. 1a, in a X-Y graph, illustrates the optical penetration depth in the skin according to radiation wavelength.

Near infrared radiation (NIR) can penetrate from 0.7 to 30 mm into tissue. NIR from 750 to 3000 nm can typically induce molecular vibration that manifest themselves as temperature increases. It has been hypothesized that using wavelengths most absorbed by water may allow to preferably heat deeper skin tissue layers as the upper skin tissue layers are typically dehydrated (much lower water content in epidermis). For example, as seen in FIG. 1a, wavelengths of 850-990 nm are relatively well absorbed by water while penetrating relatively deep into the skin. They are also relatively easily produced at relatively high irradiance using currently available technology.

The absorption of radiation in the infrared region results in molecular rotations when the rotation of the whole molecule is done about some axis and molecular vibrations when the stretching or bending of bonds result in the displacement of atomic nuclei relative to each other, without affecting the equilibrium positions of nuclei. Infrared radiation would not be expected to cause chemical changes in most molecules, although reaction rates might be increased due to heating.

Generally, the invention described herein relates to a method of drug delivery through the skin, and other applications of localized skin heating, wherein radiant infrared (IR) is used to raise skin tissue temperature to promote better drug penetration, or for other applications. For example, it was observed that under some conditions, heating the sub-epidermal layers of skin induce a mechanical enlargement of pores and allows, among other applications, to deliver substances within the hair follicle and sebaceous/sweat glands. This concept can be used as a novel skin preparation before PDT (Photodynamic Therapy) and/or when a challenge relates to the modulation of pore size as a potential route for drug delivery. It has been hypothesized, without limiting the claimed invention to such a hypothetical mechanism, that radiant IR, by increasing skin temperature, provides skin pores dilatation, allowing photosensitizers to reach targeted structures. As an example, a typical infrared sauna session performed in accordance with the invention causes a brief 1-3 degree(s) increase in body temperature.

Human skin can absorb IR because of its deep penetrating ability. When IR penetrates through the skin, the light energy is transformed, at least in part, into heat energy. The thermal effect within the relatively deep layers of tissues causes blood vessels in capillaries to dilate and the heat produced induces pores to enlarge, typically in order to eliminate resulting body toxins and metabolic wastes through sweating. The enlargement of pores, especially in pore dense areas implies a potential to enhance substance penetration at the site of heating and to increase drug concentration in the heated tissues and adjacent anatomical structures. The applicant found the new and unexpected result that heating the skin tissues from within, in other words heating first the sub-epidermal layers and letting the heat be conducted to adjacent tissue structures, produced enhanced substance penetration as compared to methods in which heat is applied to the epidermal layer by conduction or convection to deeper structures.

Pore size can be associated to apocrine gland metabolism. Briefly, the skin is supplied with sensory and autonomic nerves. Sensory and autonomic nerves differ in that sensory nerves possess a myelin sheath up to their terminal ramifications, but autonomic nerves do not. The autonomic nerves, derived from the sympathetic nervous system supply blood vessels, the arrectores pilorum, and the eccrine and apocrine glands. On the other hand, sebaceous glands possess no autonomic innervations and their functioning depends on endocrine stimuli (Walter F Lever, Gundula Schaumburg-Lever, *Histopathology of the skin,* 7th Editions, 1990. p 33.) IR induced heat then has a potential to influence sweat glands and pore size by signaling through autonomic nerve endings.

IR induced drug absorption in the skin focuses on the promotion and enhancement of the passage or flow of a substance, compound or photosensitizer leading towards a target structure, for example the sebaceous glands, among other possibilities. In at least one aspect of the present invention, once the substance, compound or photosensitizer reaches threshold concentration in the relatively well confined skin targeted structure, another light source (typically of a different wavelength depending on the peak absorption of that compound or photosensitizer or other parameter) would then be used to photochemically activate the newly absorbed and confined drug to achieve the expected clinical outcome. However, in alternative embodiments of the invention, there is no need to photochemically activate the substance.

An aim of the proposed method is to facilitate/allow movement/penetration of a photosensitizer before its photoactivation by a light source as part of the Photodynamic Therapy (PDT) procedure. The invention described herein involves radiant infrared pre-PDT skin preparation. Some IR wavelengths usable in such applications are relatively well absorbed by water, have relatively little/low epidermal melanin absorption, provide a relatively deep dermal penetration, and are not readily absorbed by the photosensitizer used. The proposed mechanisms of action are to: 1—increase pore size and 2—induce vibrational/rotational alterations in the diffusion kinetics of chemical mediators to increase drug penetration across the epidermis and part of the dermis in order to reach dermal targeted skin structures (i.e. pilosebaceous apparatus). The proposed method increases delivery in the skin to targeted structures such as sebaceous glands. Radiant IR LED light is used to open the pore, triggering a localized physiological opening of the ostium. According to selected treatment parameters, this reaction, while not immediate, typically takes place over 10-30 min to increase cutaneous temperature substantially and uniformly, allowing better mechanical opening of the ostium and simultaneously improving the metabolic ability to absorb the photosensitizer photobiochemically. The radiation is absorbed by water present in the irradiated tissue, resulting in a substantially uniform increase the cutaneous temperature and in the heat being given off and migrating from the inside of the cutaneous tissue to the outside environment (inside-out heat dissipation). Since there is relatively little water present in the upper layers of the skin, the radiation is mostly absorbed in sub-epidermal tissues. This causes various changes in the skin, such as opening of skin pores, and allows the photosensitizer or other substance to penetrate into the skin. It should however be understood that other types of applications of the proposed method could be used without departing from the scope of the present invention.

To provide IR radiant irradiation with relatively low level radiant near-IR exposure before photosensitizer incubation, light emitting diodes (LED) offer several advantages: good control on beam uniformity, sufficient power, no direct contact required as in conductive heat, no interference with active medium (air, water) as in convective heat, easy modulation technically, large surface, relatively narrow bandwidth (for example 30 nm or less) and relatively high reliability. As opposed to conductive and convective heat, radiant heat is quite different. Radiant heat is given off from a heated body following IR irradiation. For the skin, it means that heat generated from the absorption of water within the dermis (sub-epidermal layer) especially water located in the ECM (extracellular matrix) is migrating from the inside to the outside environment progressively.

Figure 5:
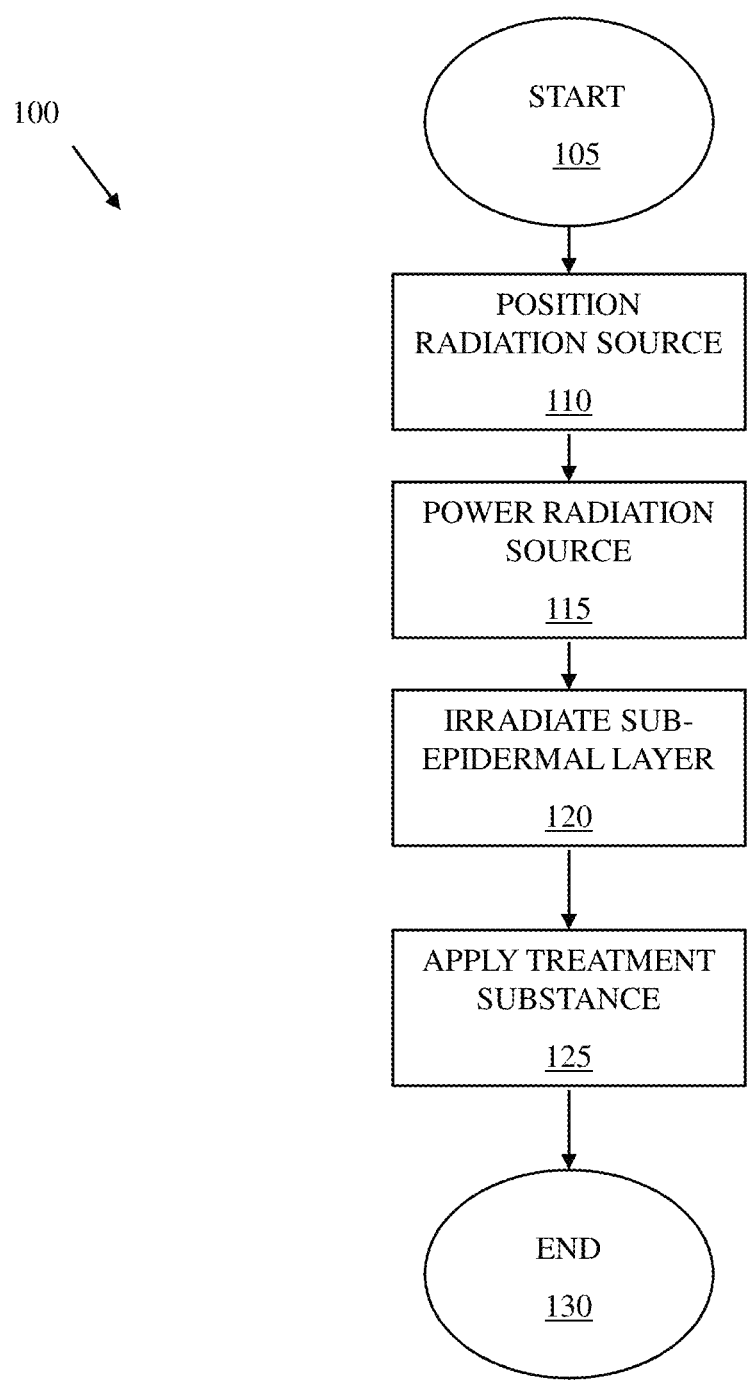
FIG. 5, in a flowchart, illustrates a method for treating skin tissues in accordance with an embodiment of the present invention.

An example of a method 100 for treating skin tissues is shown in FIG. 5. The method begins at step 105. At step 110, a radiation source is positioned outside of the skin tissues at a predetermined distance from the skin surface. At step 115, the radiation source is powered so as to produce infrared radiation having a predetermined spectrum and a predetermined power. Then, at step 120, the sub-epidermal layer is irradiated with the infrared radiation through the epidermal layer, the predetermined spectrum and the predetermined power being such that the infrared radiation is absorbed to a larger degree in the sub-epidermal layer than in the epidermal layer. In some embodiments of the invention, at step 125, the method 100 includes applying a treatment substance on the skin surface. In some embodiments, the treatment substance includes a photo-activatable substance, and step 125 then further comprising irradiating the skin tissues with radiation having a spectrum and a power density suitable for activating the photo-activatable substance. Finally, the method ends at step 130.

While in the proposed method the radiation is mainly absorbed in the sub-epidermal layer, there remains a possibility that a minor portion of the radiation be absorbed in the dermis and produce photobiochemical changes in this skin layer contributing to the observed physiological effects.

EXAMPLES

Under different parameters (wavelength (nm), power density (mW), intensity (mA), mass (Kg), distance (cm) and treatment area), the amount of time required to start noticing a heat induced pore size increase/enlargement was identified in many subjects. Two wavelengths were selected with respect to the water absorption spectrum in the IR. Radiant skin heating can occur with light sources emitting at various wavelengths. For instance, while little water absorption is seen at 870 nm with deeper dermal penetration, a strong absorption is described at 970 n—about eight times more—at the expense of less penetration depth (FIG. 1a).

Figure 1B:
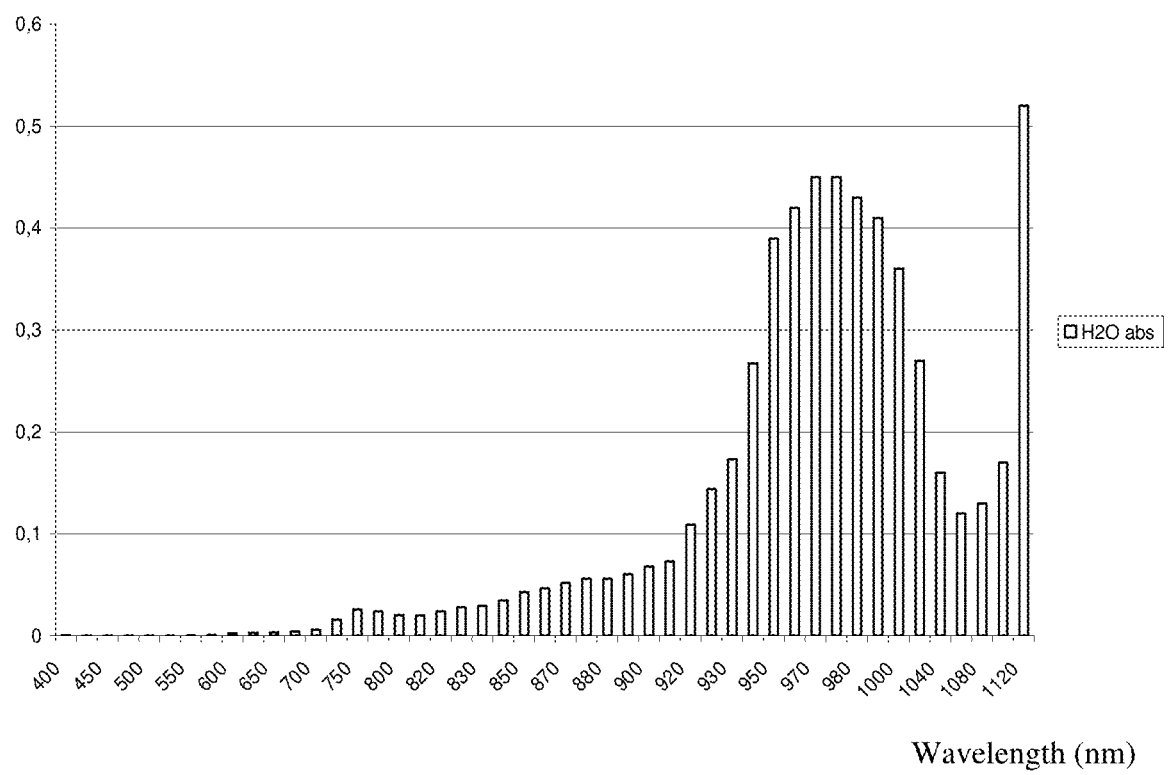
FIG. 1b, in a bar chart, illustrates the water absorption curve as a function of radiation frequency.
Figure 1C:
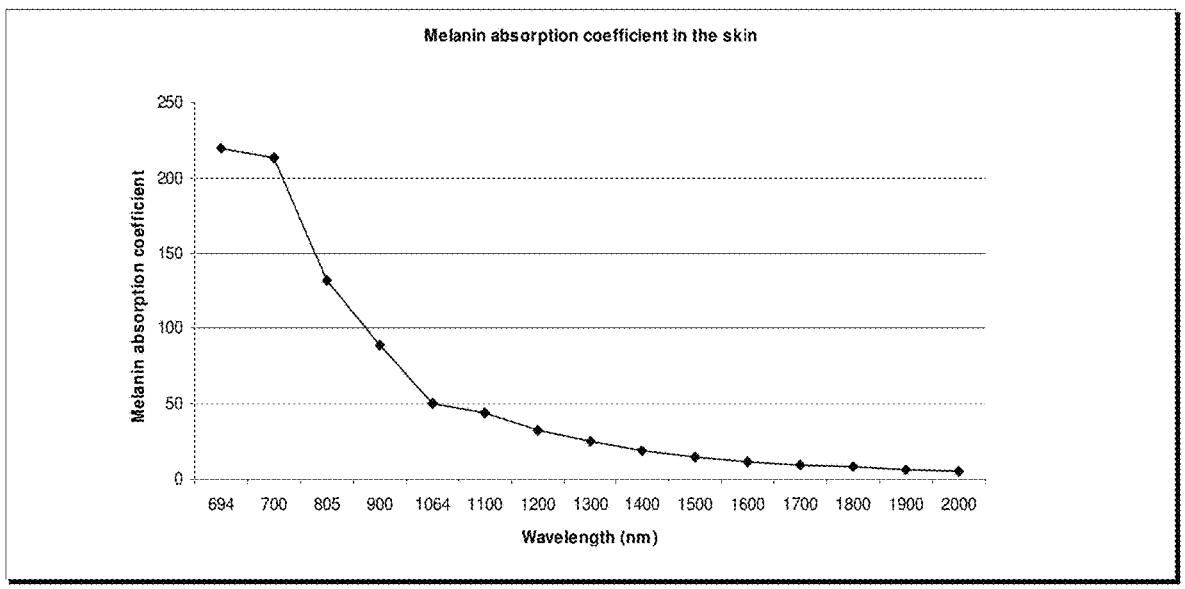
FIG. 1c, in a X-Y graph, illustrates the melanin absorption curve as a function of radiation frequency.

However, the entire spectrum of the water absorption curve (FIG. 1b) can be used for radiant skin preparation, according to selected treatment parameters. Moreover, this pre-treatment procedure is suitable for all skin phototypes due to relatively low melanin interference (FIG. 1c).

The treatment distance must be adapted to participant's anatomy, but a minimal distance between the light source and the participant's skin surface must be maintained to avoid possible burns. The treatment distance is to be determined according to the source power density, measured with the light intensity reaching the treatment area (skin surface).

Example 1: Radiant IR Increases Skin Temperature and Opens Skin Pores (Anterior Arm)

A thermocouple type-T probe (Omega inc.) was inserted at the papillary junction of the skin (D-E (dermo-epidermal) junction) of the anterior arm of a subject to allow real time measurements of skin temperature during IR exposure. Preliminary testing performed on an ex vivo animal model had shown a significant increase in temperature using radiation of 870 nm, at 80 mW/cm$^2$, with a source 3 cm away from the target area for exposures up to 30 minutes (resulting in a fluence of up to 144 J/cm$^2$) (data not shown). The human model (in vivo) testing described herein considers superior tissue mass (bulk effect) and inherent physiological body temperature management mechanisms (i.e. blood capillaries heat dissipation) that could influence the temperature variation monitored by the probe during IR exposure.

Figure 2:
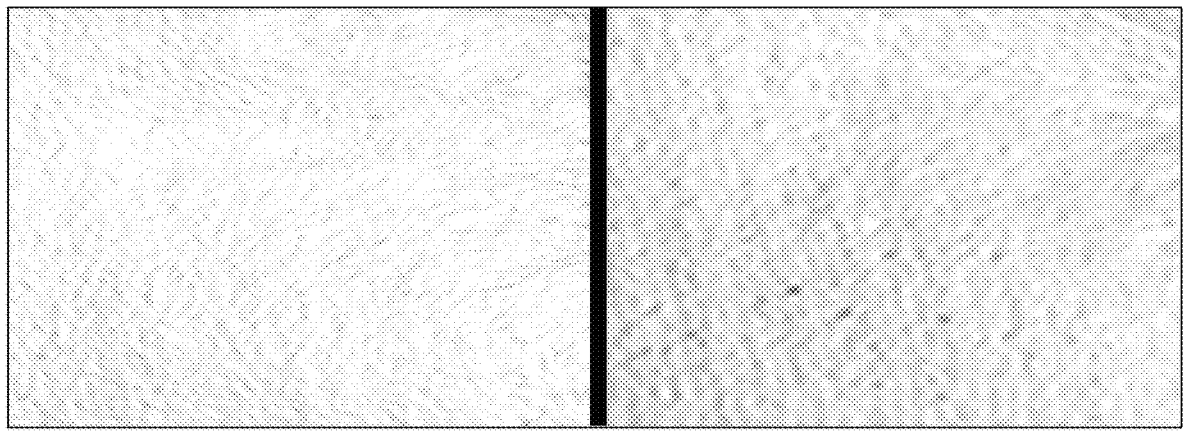
FIG. 2 illustrates skin texture with Primos 3-D Microtopographies of upper middle back skin before and after radiant IR skin preparation, as well as 5 and 20 minutes post-treatment.
Figure 2:
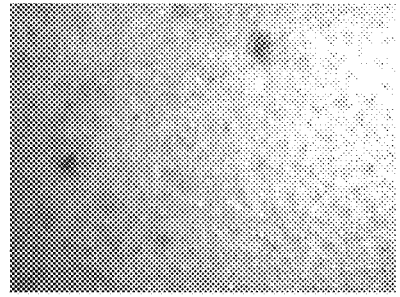
Figure 2:
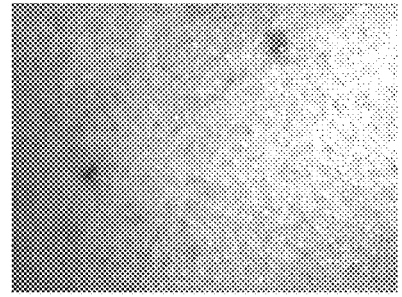

Two sets of parameters were investigated: 870 nm at 200 mW/cm$^2$ (High Irradiance) and 970 nm at 50 mW/cm$^2$ (Low Irradiance), at a treatment distance of 2.5 cm. Treatment time determined the fluence (irradiance X time=fluence). The objective was to reach a dermal skin temperature between 38-41° C.; 41° C. being the maximum as 42° C. may induce cellular injury or enzymatic dysfunction and pain being felt at 45° C. For both sets of parameters, irradiation time lasted 11 minutes and the following readings were observed: at 870 nm a light source irradiating at 200 mW/cm$^2$ lead to a 33 to 40° C. temperature increase (Δ 7° C.), while 50 mW/cm$^2$ irradiating at 970 nm lead to a temperature increase of Δ 6° C., from 31 to 37° C. Finally, fine scale monitoring using the PRIMOS 3D-microtopography system (GFM, Germany) showed pore size enlargement and opening post-treatment (FIG. 2).

Example 2: Radiant IR Skin Preparation: Temperature and Sebum Monitoring

Figure 3:
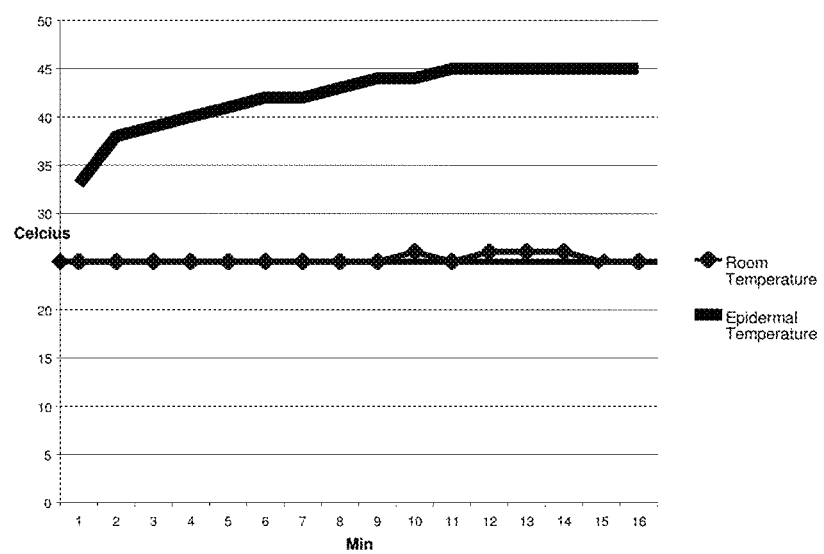
FIG. 3, in a X-Y graph, illustrates epidermal and room temperature during the treatment of the middle upper back of a subject during 15 min of irradiation with 870 nm IR light, which delivered 117 J, at a 2.5 cm treatment distance (130 mW/cm2, Mode: continuous wave (CW))
Figure 4:
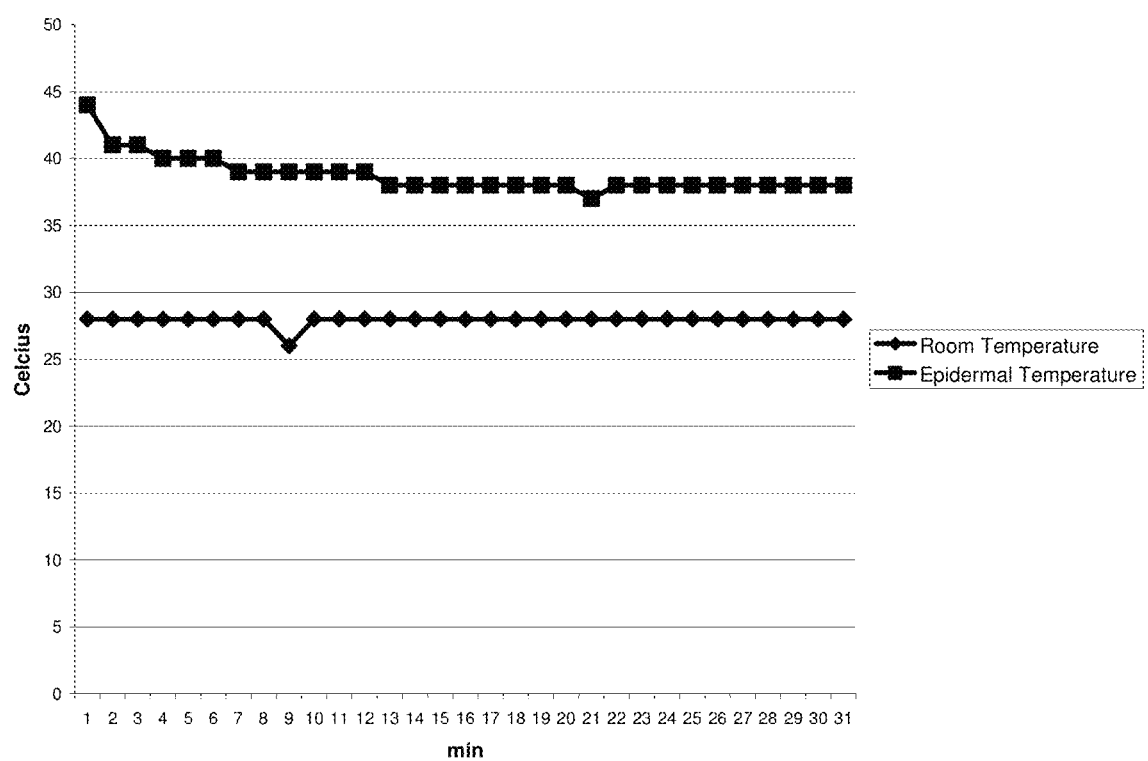
FIG. 4, in a X-Y graph, illustrates epidermal and room temperature after the treatment for which the results are shown in FIG. 3.

The treatment area, the middle upper back, was cleaned with a mild soap 60 min prior to the experiment. Sebum measurement was assessed with a dermaspectrometer and temperature was monitored with a thermocouple (Omega inc.). Then, 15 min of 870 nm IR light, delivered 117 J, at a 2.5 cm treatment distance (130 mW/cm2, Mode: continuous wave (CW).). Sebum readings using a sebumeter SM815 (CK electronic GmbH) were taken prior to irradiation (T0), after 15 min irradiation time (T15), right after the acetone scrub (Ta), after the second 15 min irradiation time (T215), and at 30 min cool off time (Tc30). The following readings were measured on the upper back: T0: 8; T15: 13; Tc30: 11. Periodic epidermal temperature was monitored every minute during IR exposure using a type T thermocouple firmly resting on the epidermis, in the middle of the treatment area on the upper back. Temperature was monitored every minute. During this experiment, room temperature was held constant (25-26° C.). Cool off (30 min), once the second IR exposure was performed, epidermal temperature was monitored for 30 min on the treatment area, going from 44 Celsius to 38 Celsius over 30 min while room temperature remained constant (data not shown). Sebum liberation and epidermal temperature readings were monitored during the experiment and during a 30 min cool off, as seen respectively in FIGS. 3 and 4. After 15 minutes of IR exposure, the skin temperature went from 33 to 45° C. and sebum production nearly doubled (FIG. 3). Cool off showed a relatively slow decrease of skin temperature as skin went from 44 to 38° C. in 30 min (FIG. 4). Inside-out radiant IR skin preparation heats the skin substantially uniformly and triggers a tissue response leading, among others, to the opening of skin pores. Once the temperature response is stable for several minutes (45° C. plateau), it is unlikely that an additional short IR burst would change the absorption rate of the photosensitizer since the process has already reached the threshold of activation triggering a cascade of events. The cool-off phase following the first IR exposure is sufficient for this reaction to happen. Erythema (redness) was seen after the first IR exposure and remained after a 60 min cool off time—a soothing moisturizing cream was applied on the treated area to make it more comfortable. This could be related to a blood capillaries vasodilatation phenomenon. Finally, no residual erythema was observed 24 hours post-treatment, following a single 10-30 min IR exposure. The radiant IR skin preparation objective is for the pores to open, for the sebum to vanish and the photosensitizer to get inside. It is better to let the skin cool-off relatively slowly and let the pores return progressively to their 'before' treatment configuration during photosensitizer incubation. It is important to note that IR light did not induce any pain during treatment. After a 5-10 min IR exposure time, some light shivering occurred (goose bumps). This phenomenon could involve an attempt to regulate body temperature. Inside-out radiant heat using near-IR appears is a unique method to increase cutaneous temperature uniformly, allows mechanical opening of the ostium and seems to improve the absorptive ability of the photosensitizer photobiochemically.

Example 3: IR Skin Preparation Leads to Temperature Increase (Middle Upper Back) Enhancing PDT Treatment Outcome in an Acne Patient A treatment was carried on a 32-year-old female suffering from mild inflammatory acne in the upper back. Briefly, the treatment area was cleaned with a mild soap and an acetone scrub was performed. The IR-device (870 nm, 130 mW/cm$^2$, Mode: CW) was placed over the treatment area (middle upper back). A distance gauge maintained the treatment distance at 2.5 cm during the entire procedure. Then, the treatment area was exposed to the IR LED device for 15 min and 177 J were delivered. After the radiant IR skin preparation, the treatment area and the photosensitizer, kept at room temperature, was applied for 90 min. Then, 5-aminolevulinic acid (Levulan™ Kerastick™) was activated by red LED light delivered by the LumiPhase-R (Opusmed, Canada), for 20 min. Finally, a 5 min exposure at 405 nm LED 30 mW/cm$^2$) was performed. Her back was then washed-off and the patient was instructed of post-PDT treatment precautions. This treatment proved successful and acne lesions were significantly reduced (≥50% clearing acne lesion count) after a single treatment.

Example 4: Split-Face Use of Radiant IR Skin Preparation Prior to a PDT Treatment for Diffuse Sebaceous Glands Hyperplasia A PDT treatment was performed on the face of a 39-year-old male patient suffering from diffuse sebaceous gland hyperplasia. He was complaining of redness exacerbated by exercise/effort. The patient showed oily skin, dilated pores and multiple confluent sebaceous hyperplasia lesions. Facial lesions were distributed mainly on the forehead and cheeks. This condition was progressing since his late 20s and was relatively stable. He applied only topical Metrogel. Clinical examination showed multiple whitish 0.5 to 1 mm diameter well circumscribed, uniformed and yellowish elevated papules. Also, comedones and papulo-pustules were present. The patient was skin phototype II (Fitzpatrick classification) . His father had similar skin condition.

Sebaceous gland hyperplasia (SH) shows a wide spectrum of clinical and histopathological features and the etiology of diffuse sebaceous gland hyperplasia remains unknown. Treatment of sebaceous hyperplasia is mostly performed for cosmetic reasons. While circumscribed lesions vary in size and color, diffuse facial sebaceous gland hyperplasia shows large, flesh-colored or whitish papules often with central umbilication. The patients look extremely oily, in contrast to those with the circumscribed sebaceous hyperplasia variant. Treatment options available for the circumscribed type are mostly mechanical. Lesions tend to recur unless the entire unit is destroyed or excised. Risk of permanent scarring must also be considered. Other therapeutic options include cryotherapy (liquid nitrogen), cauterization or electrodesiccation, topical chemical treatments (e.g., with TCA), laser treatment (e.g., with carbon dioxide or dye laser), shave excision, and surgical excision. Patients can also be treated with low dose of systemic isotretinoin (13-cis-retinoic acid) which can result in complete or substantial clearing. However, due to side effects, the use of isotretinoin is usually suggested only when other therapies are unsuccessful or unamenable, or as a temporary relief for patients with multiple/diffuse sebaceous hyperplasia lesions. In fact, clearing resulting from oral isotretinoin uptake will not last if medication is ceased.

Prior to PDT, radiant IR skin preparation was performed in only half of his face (split face study). Then PDT was completed on the complete facial area. First, the face was washed with a mild soap and an acetone scrub was performed. A 970 nm LED source prototype emitting at 50 mW/cm2 in a CW mode was placed at 1.5 cm from the right side of his face and left for 25 min. Right after split face irradiation, 5-aminolevilinic acid (Levulan™ Kerastick™) was applied to the treatment area and left for 90 min. The photosensitizer was then light activated by a 630 nm LED source emitting at 50 mW/cm$^2$ (LumiPhase-RB, Opusmed, Canada), until erythema was reached (20 min). This treatment was concluded by a 405 nm LED source emitting at 30 mW/cm$^2$ (LumiPhase-RB, Opusmed, Canada), for 5 min. Follow-up appointments revealed 50% clearing of SH lesions after a single treatment on the pre-treated side (radiant IR skin preparation side). The other side showed only a 30% improvement. Through a mechanism involving the opening of skin pores, IR radiant skin preparation enhanced drug penetration and absorption by the targeted structures (i.e. sebaceous glands). Clinically, skin texture was significantly improved on the IR pre-treated side.

For this patient, such effective PDT treatment was an interesting alternative to systemic therapy involving possible side effects. Clearing was maintained up to 6 months post-treatment especially on the radiant IR pre-treated side. Risks related to the study were relatively low as treatment effects were strictly limited to the area of skin to be tested and were relatively unobtrusive: redness similar to what can be observed in a mild sunburn.

Example 5: Split-Face Radiant IR Skin Preparation Prior to a PDT Treatment for Actinic Keratosis of the Face and Scalp A 72-year-old male was treated for actinic keratosis lesions on the face and scalp. After performing an acetone scrub on the treatment area, a radiant IR skin preparation was done on the right side of his face (970 nm, 40 mW/cm2, for 30 min). The usual PDT protocol was then resumed, with a 90 min 5-aminolevulinic acid (Levulan™ Kerastick™) incubation. To activate the photosensitizer, a 630 nm CW (150 mW/cm2) light was first used for 13 min. A 5 min, 405 nm CW blue light exposure (30 mW/cm2) completed this procedure. Right after treatment, the side pre-treated with IR exhibited twice as much erythema (tissue visual end-point) as the untreated side. Results showed enhanced clinical improvements on this side (right) as well as skin texture restoration with 60% lesion clearance, compared to 40% on the left side after a single PDT treatment.

Example 6: Split-Face Radiant IR Skin Preparation Prior to a PDT Treatment for Inflammatory Type Acne of the Face A 22-year-old male was treated for facial papulo-pustular inflammatory acne lesions. After performing an acetone scrub on the treatment area, a radiant IR skin preparation was done on the right side of his face (970 nm, 80 mW/cm2, for 30 min). Then 5-aminolevulinic acid (Levulan™ Kerastick™) was applied to the skin and left for 90 min incubation time. Subsequently, to activate the photosensitizer, a 630 nm CW (50 mW/cm2) light was first delivered for 15 minutes followed by 405 nm CW blue light exposure (30 mW/cm2) for 5 minutes to complete the treatment. At follow up, results showed enhanced clinical improvements on the IR treated side as lesion count was significantly reduced (60-70% lesion number reduction) after only one treatment, as oppose to the untreated side which needed an additional PDT session to achieve similar results (one month later). Radiant IR skin preparation allows for a reduction in the number of PDT treatments necessary for significant clinical improvements.

Example 7: Photopreparation

Introduction

Photopreparation is a new concept that we have been working on which characterizes a way to enhance the delivery, through a substantially uniform penetration, of a given compound in the skin in order to get more active conversion of such topical agents (i.e. ALA to PpIX) in targeted tissues. Radiant IR photopreparation increases skin temperature which may lead to an increment in pore size (diameter) for enhanced penetration of a given topical in the pilosebaceous unit. In this specific example, a pre-PDT use of radiant infrared LED exposure as skin preparation to enhance cystic acne treatment outcome is investigated.

Background and Objectives

PDT treatment efficacy for acne is highly dependent on optimal absorption of topical agent within the dermis. Inadequate activation of the photosensitizer at the targeted dermal structures, such as the sebaceous glands, has led to variability in clinical results obtained. Herein, a radiant infrared skin preparation (inside-out radiant heat energy generation) was used prior to PDT so as to enhance delivery of topical agent and photoactivation to the sebaceous glands of cystic acne patients.

More specifically, an alternative approach in the treatment of inflammatory type acne is photodynamic therapy (PDT) with 5-aminolevulinic acid (5-ALA). ALA-PDT increases the endogenous synthesis of protoporphyrin IX (PpIX), a potent photosensitiser. The efficacy of ALA-PDT is dependent on ALA absorption and remains one of the main challenges of PDT.

Study Design/Materials and Methods: Eleven (11) patients were enrolled in a split face or split back (pre-treated side versus control) study with a pre-approved IRB protocol. Patients exhibiting cystic acne with a lesion count of at least 10 were selected. Lesion count was assessed both manually and by digital photography before and 4 weeks after one PDT procedure. Prior to the application of 5-ALA, one side of the face or back was pre-treated with radiant IR [CW LEDs emitting @λ 970 nm, irradiance 50 mW/cm2 for 15 minutes, total fluence 45 J/cm2], while the other half was used as control. PDT was then performed on the entire surface (face or back).

Results: According to our dual (manual and digital) lesion count analysis, a statistically significant decrease in the number of cystic lesions was observed on the pre-treated versus control side one month after PDT for most patients. Data will be discussed.

Conclusion: Proposed mechanisms of action are induction of vibrational/rotational alterations in the transcutaneous diffusion kinetics of photosensitizer and/or enhanced conversion of 5-ALA to PpIX at higher temperature. Pre-PDT radiant IR LED exposure is a promising tool to enhance PDT efficacy especially for resistant cystic acne lesions.

Example 8: Photopreparation

It has recently been shown that increased skin temperature during topical ALA application can enhance the conversion of 5-ALA to PpIX in skin deeper layers. These results support increasing the skin temperature before ALA-PDT in the treatment of acne. Radiant infrared (IR) is known to rise skin temperature via inside-out dermal water absorption and thus may be useful in PDT-ALA to promote ALA absorption and its conversion to PpIX. The present study was conducted to test this hypothesis in the treatment of cystic acne. We have also previously studied the advantage of using red and blue light in combination to enhance PDT results and test more specifically the combination of two activation of substances with any other.

Figure 6:
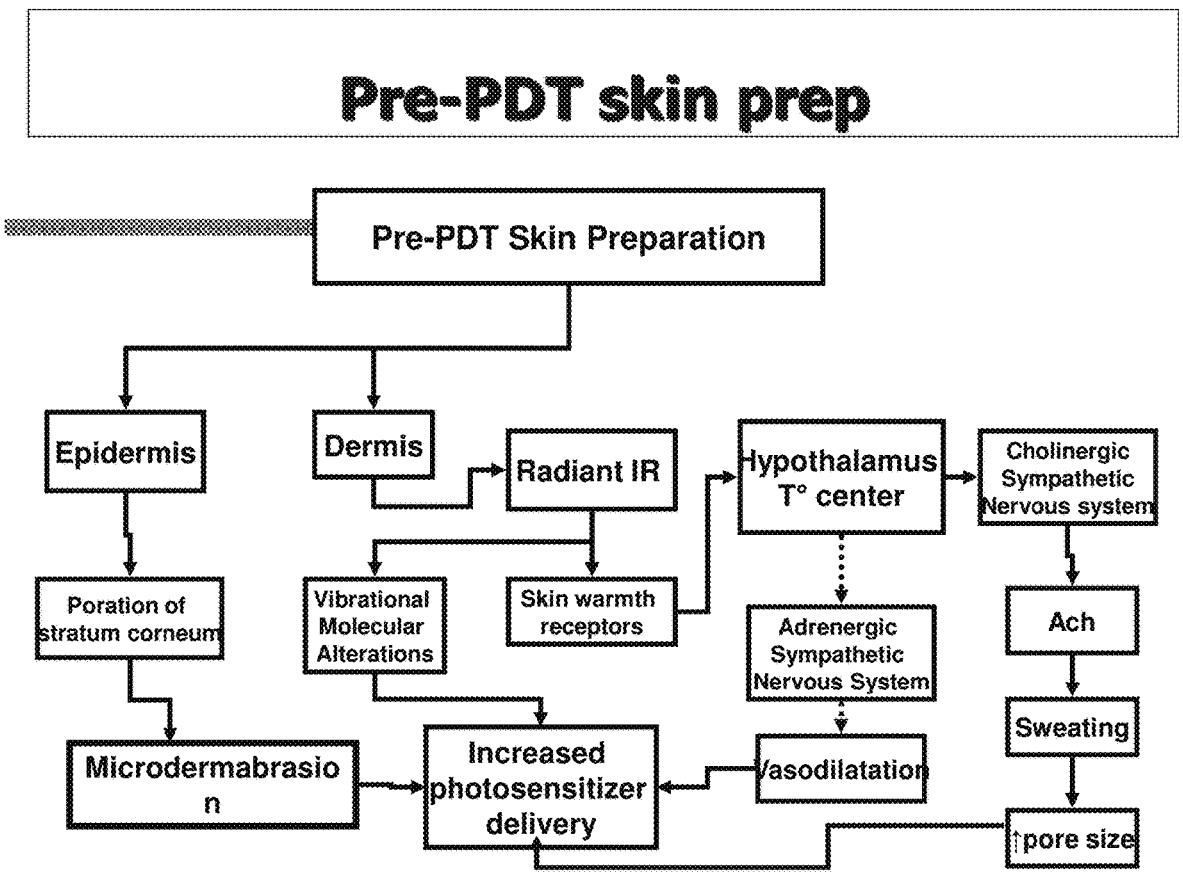
FIG. 6 illustrates in a flowchart hypothesized mechanisms thought to be involved in this improved method.

Without restricting the scope of the invention, it is believed that possible mechanisms of action of the proposed method include one or more of an increase pore size, the induction vibrational/rotational alterations in the diffusion kinetics of chemical mediators, modification of vascular responsiveness and cellular repair processes an increase conversion of 5-ALA to PpIX at higher temperature. Indeed, the absorption of radiation in the infrared region results in molecular rotations (rotation of the whole molecule about some axis) and molecular vibrations (the stretching or bending of bonds resulting in the displacement of atomic nuclei relative to each other, but not affecting the equilibrium positions of nuclei). Infrared radiation would not be expected to cause chemical changes in molecules, although reaction rates might be increased due to heating. Therefore, the above suggests large surface controlled narrow spectral band irradiation to increase skin temperature & possibly induce transitory molecular alterations to facilitate/allow penetration of a photosensitizer like 5-ALA. FIG. 6 illustrates in a flowchart hypothesized mechanisms thought to be involved in this improved method.

Study Design/Materials and Methods

In summary, ten patients were enrolled in a split face or split back (pre-treated side versus control) study with a pre-approved IRB protocol. Patients exhibiting cystic acne with a lesion count of at least 10 were selected. Lesion count was assessed both manually and by digital photography before and 4 weeks after one PDT procedure. Prior to the application of 5-ALA, one side of the face or back was pre-treated with radiant IR [CW LEDs emitting @λ 970 nm, irradiance 50 mW/cm2 for 15 minutes, total fluence 45 J/cm2], while the other half was used as control. PDT was then performed on the entire surface (face or back) using 5-ALA in a conventional manner.

More specifically 10 patients (7 Male, 3 Female; age 13-54) exhibiting cystic acne with a lesion count of at least 10 were enrolled. Patients were assigned to a split face or split back group. One side was pre-treated for 15 minutes with radiant IR [CW LEDs emitting @λ 970 nm, irradiance 50 mW/cm$^2$, total fluence 45 J/cm$^2$] to obtain a temperature of about 42 Celcius, while the other side was used as control. ALA was then applied after which PDT was performed on the entire face or back surface. Lesion count was assessed manually and by digital photography, before and 4 weeks after the PDT procedure. Exclusion criteria were: current use of the following medications: (Prednisone), anticoagulant therapy, drugs known to cause photo-sensitivity reactions. In addition, during 12 months preceding the study, subjects are required not to take Accutane (isotretinoin); use of corticosteroids on the treated area within 2 weeks of first treatment; use of topical tretinoin (like Retisol-A, Retin-A, Vitamin A acid, Retin-A micro) for at least 1 month prior to enrollment; yanned skin around or on the area to be treated: the back. previous laser of medicated treatment at the treatment site (to be studied) and for the duration of the study; presence of any known diseases among vitiligo, psoriasis, severe eczema, poor skin healing. active infection, immunosuppression, coagulation problem, peripheral arterial disease, hematologic abnormalities, vasculitis, and previous history of epilepsy; pregnancy; alcohol or drug abuse before and during the study.

After the pre-treatment with IR radiation, 5-ALA was applied onto slightly abraded skin and left to incubate for 60 minutes on both IR-pre-treated and control sides. Then, the 5-ALA treated regions were irradiated with a LED source of red light (wavelength of 630 about 30 min, in accordance to standard therapy, until a mild to moderate erythema appeared. Immediately afterwards, the 5-ALA treated regions were irradiated with a LED source of blue light (wavelength of 405 nm, power density 30 mW/cm$^2$) in continuous wave mode for 3 min.

Results

According to our dual (manual and digital) lesion count analysis, a statistically significant decrease in the number of cystic lesions was observed on the pre-treated versus control side one month after PDT for most patients. A significant decrease in the number of cystic lesions was observed on the pre-treated (72.5%) versus the control side (47.1%) one month after PDT (t=4.55, p<0.001). No treatment-related adverse effects were reported. More specifically, the mean+/−standard error number of lesions before treatment was 49.7+/−13.7 on the IR treated site and 35.9+/−8.3 on the control side. After treatment, the mean+/−standard error number of lesions was 12.0+/−2.3 on the IR treated site and 16.3+/−3 on the control side.

Conclusion

Proposed mechanisms of action are induction of vibrational/rotational alterations in the transcutaneous diffusion kinetics of photosensitizer and/or enhanced conversion of 5-ALA to PpIX at higher temperature. Pre-PDT radiant IR LED exposure is a promising tool to enhance PDT efficacy especially for resistant cystic acne lesions.

Example 9

Acne vulgaris is a common skin disease characterized by the formation of comedones, erythematous papules and pustules and, in some cases, nodules or cysts [$^i$]. Aside from scarring, its main effects are psychological with reduced quality of life and self esteem. Conventional topical or oral medications such as antimicrobials, anti-inflammatory agents, hormones and retinoids, target the pathogenetic factors of acne with variable success and can be inconvenient and have side-effects.

*Propionibacterium acnes* (*P. Acnes*) is a gram-positive non-sporulating bacterium which is found in human sebaceous glands and known to play an important role in the aetiology of acne [$^{ii}$] Studies have shown that *P. acnes* is able to produce protoporphyrin IX (PpIX) and that application of the photosensitizing agent 5-aminolevulinic acid (ALA) leads to enhanced PpIX accumulation [$^{iii}$, $^{iv}$, $^{v}$]. ALA induced PpIX production in human skin is located in the epidermis but also in sebaceous glands and hair follicles [$^{vi}$, $^{vii}$, $^{viii}$]. Photoactivation within a specific range of wavelengths of this photosensitizer has been shown to lead to eradication of *P. acnes* and destruction of the pilosebaceous unit [,$^{ix}$, $^x$]. This approach, named photodynamic therapy (PDT), is based on photochemical reactions mediated through the interaction of photosensitizing agents, light and oxygen, during which cytotoxic reactive oxygen species are formed causing damage (necrosis, apoptosis) to the target structures. Topical PDT has been found to be efficacious in the treatment of acne vulgaris with various light sources, treatment regimens, and photosensitizers [$^{xi}$, $^{xii}$, $^{xiii}$].

The success rate of topical-PDT is dependent on optimal penetration of the topical agent and subsequent PpIX production. Topical-PDT efficacy may be limited by the rate of ALA uptake into the cells and/or its penetration through the tissue due to its hydrophilic properties. The many studies investigating transdermal drug administration indicate that skin heating prior to or during topical application of a drug will dilate the skin's penetration pathways, increase kinetic energy and the movement of particles in the heated area, and facilitate drug penetration [xiv]. Temperature percutaneous penetration enhancement has been observed with several topical compounds and might also apply to ALA [xv, xvi, xvii]. Elevating the local skin temperature in order to increase the penetration of ALA into the skin, which thereby may increase PpIX production, could represent another approach to improving ALA-PDT of acne lesions.

The impact of temperature during ALA incubation on ALA penetration and PpIX production has been investigated in a number of in vitro and in vivo studies. The evidence shows that ALA-induced PpIX formation is a temperature dependent process where significant amounts of PpIX are formed after photosensitizer application at high skin temperature (36-42° C.), whereas very little or no PpIX production takes place when the skin is cooled (12-18° C.) [xviii, xix, xx, xxi, xxii]. There is also some indication in the literature that raising temperature above the normal skin physiological level (32° C.) during ALA incubation enhances ALA uptake, exceeding that anticipated for simple diffusion, [xxiii]. Results from these studies, however, are in contrast with other experiments showing that ALA penetration into the skin is only slightly dependent on the skin temperature. These experiments assumed, however, that separate ALA uptake and PpIX formation phases can be distinguished in the skin when a short (i.e. 10 or 15 min) ALA application period is used. The effect of raising skin temperature to improve percutaneous penetration of ALA prior to ALA incubation has yet to be documented.

SUMMARY

Experiments testing the proposed method were performed as follows.

Background and Objective:

An alternative approach in the treatment of acne vulgaris is photodynamic therapy (PDT) that uses light and aminolevulinic acid (ALA) induced protoporphyrin IX (PpIX) production to eradicate *Propionibacterium* acnes found in acne lesions. PpIX formation is dependent on ALA percutaneaous penetration. In this study, to enhance ALA penetration and subsequent accumulation of PpIX, skin temperature was increased with radiant infrared (IR) prior to ALA-PDT application and compared to ALA-PDT alone in the treatment of inflammatory acne.

Study Design/Materials and Methods:

Ten patients exhibiting inflammatory acne with a lesion count of ≥10 were assigned to a split face or split back group. One side was pre-treated for 15 minutes with radiant IR light emitting diode (LED) (970 nm), while the other side was used as control. ALA was then applied after which PDT LED (630 nm) was performed on the entire face or back surface. Blinded lesion counts and clinical global assessment of severity were performed based on digital photographs before and four weeks after the PDT procedure.

Results:

This randomized, controlled and rater-blinded trial revealed a significant difference in median reduction of inflammatory lesions on the IR pre-treated (73%, 95% confidence interval (CI) 51-81%) versus the control side (38%, 95% CI 8-55%) one month after PDT (p<0.0001). Clinical assessment of severity was also significantly lower on the IR-treated side than on the control side (median 1, 95% CI 0.74-1.34 vs. 2, 95% CI 1.17-1.72). No unusual treatment-related adverse effects were observed.

Conclusion:

The reported therapeutic effects is believed to be due to enhanced induction of alterations in transcutaneous diffusion kinetics of the photosensitizer at higher skin temperature and/or conversion of ALA to PpIX. Pre-PDT radiant IR LED exposure appears to be a promising method to enhance PDT efficacy for the treatment of acne lesions. However, the proposed method should not be limited to this proposed mode of action.

Detailed Example

Figure 7:
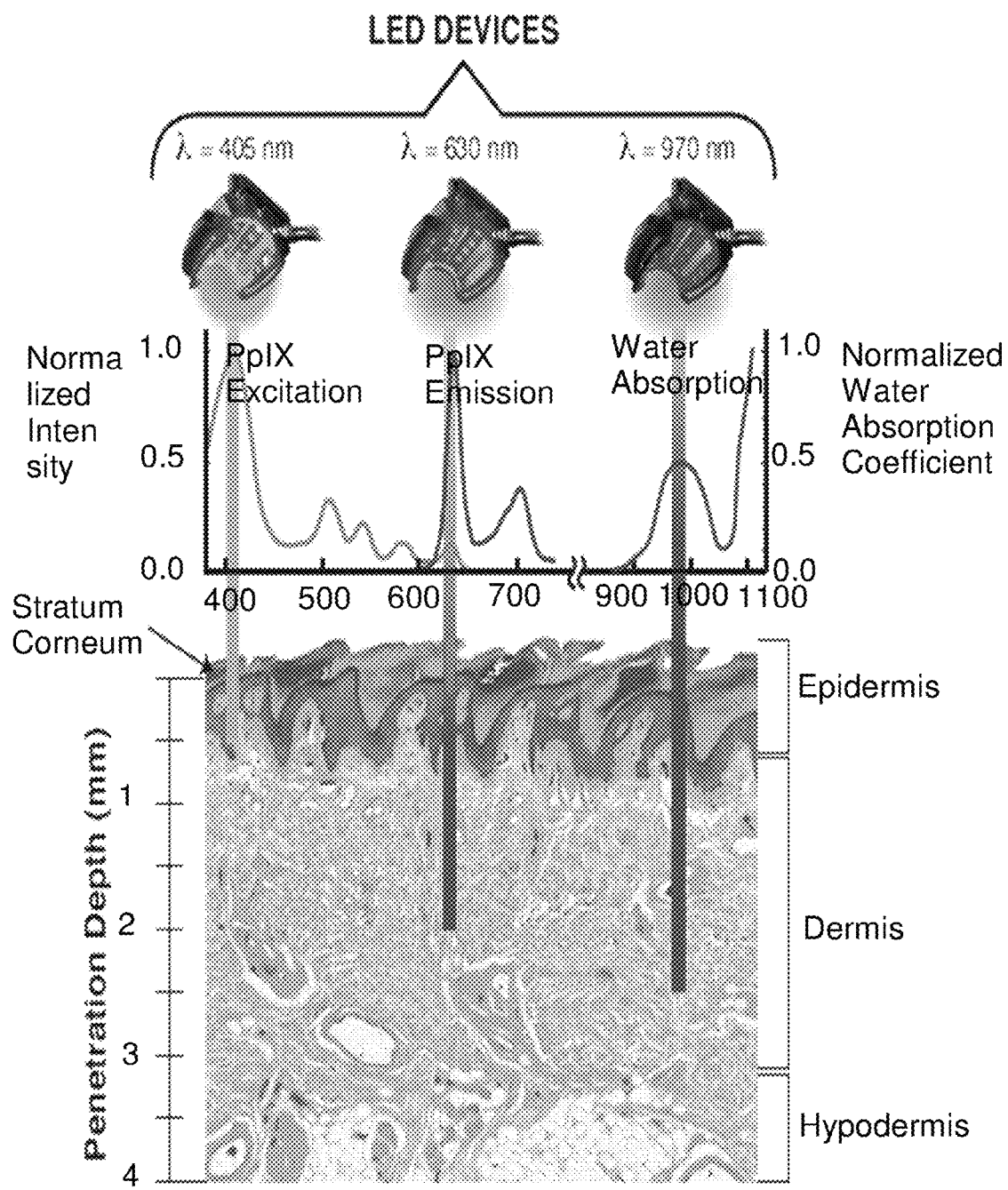
FIG. 7: Schematic representation of the penetration depth of various wavelengths in relation to fluorescence excitation and emission of protoporphyrin IX (PpIX) and water absorption coefficient. The illustration shows that, in general, the longer the wavelength (up to 970 nm), the deeper its penetration into tissues. In the skin, the penetration depth is less than 1 mm at 400 nm, of 0.5 to 2 mm between 590 and 660 nm, and 2.5 mm at 970 nm. The PpIX absorption peaks (410, 505, 540, 580 and 630 nm) are all within the visible spectrum but penetration depth is greater at 630 nm allowing enhanced photoactivation of the photosensitizer at the level of sebaceous glands during PDT. Near-IR wavelengths are well absorbed by water especially at a peak around 970 nm with the right balance of $H_2O$ absorption with optimal depth of penetration which is not possible for wavelengths >1000 nm. This in term provides a deep-seated inside-out heating of the reticular dermis for photopreparation purposes.

Exposure to radiant infrared (IR) radiation in known to rise skin temperature via inside-out dermal water absorption and may be useful in PDT-ALA to promote ALA penetration and its conversion to PpIX [xxiv]. Radiant IR photopreparation by increasing skin temperature may thus lead to improved PDT results. In the present within-patient study, the effect of radiant IR exposure using light emitting diode (LED) at 970 nm prior to ALA-PDT application was examined in the treatment of 10 patients with mild to moderate inflammatory type acne. As the PDT light source, 630 nm LED illumination was employed as it is a deep penetrating well absorbed wavelength which falls into the PpIX absorption peaks (FIG. 7) [xxv, xxvi]. It was as expected that the ALA-PDT IR pre-treated side would yield a better clinical outcome measured as the percent reduction in inflammatory acne lesion count four weeks post treatment compared to the control ALA-PDT alone treated side.

Materials and Methods

Patient Selection:

Ten (10) healthy patients exhibiting mild to moderate acne based on the Combined Acne Severity Classification [xxvii] with a lesion count of at least 10, were recruited from the Dr. Daniel Barolet Clinic in Montreal, Canada between September 2007 and February 2008. Inclusion criteria included patients with skin type I to III according to the Fitzpatrick Classification System [xxviii]. Exclusion criteria comprised patients taking cortisone (Prednisone), anticoagulant therapy, or any drug known to increase photosensitivity. In addition, during the 12 months preceding the study, patients were required not to have used isotretinoin (Accutane), or applied topical steroids on the site to be treated. Moreover, oral antibiotics use, laser or topical anti-acne medication at the to-be-treated site were not permitted for eight weeks prior to the study. Patients gave written informed consent to participate in this trial in compliance with the US Code of Federal Regulations dealing with the conduct of clinical studies (21 CFR including parts 50 and 56 concerning informed consent and IRB regulations). The study was conducted according to Good Clinical Practice Guidelines and the principles of the Declaration of Helsinki, and was approved by the Institutional Review Board Services (Div. 1373737 Toronto, Canada).

Study Procedure:

Patients were assigned to a split face or split back group to allow for within-patient assessments of clinical effects. Assignment was based on the patient's problem area. One side was randomly (using a coin flip) assigned to receive IR pre-treatment and ALA-PDT, and the other ALA-PDT alone to serve as control. The IR pre-treatment consisted of a 15 minute exposure to radiant IR LED at 970 nm (80 mW/cm$^2$, 72 J/cm$^2$ using the LumiPhase-R/IR™, OPUSMED Inc. Montreal, Canada) to reach peak $H_2O$ absorption inside-out temperature of 45° C. Papillary dermis temperature was monitored with a needle probe throughout the session and up to 40 minutes (Type-T thermocouple, Omega, Montreal, Canada). ALA (20% Levulan Kerastick, DUSA Pharmaceuticals, USA) was then applied on both sides for 60 minutes, after which PDT with LED at 630 nm (50 mW/cm$^2$, 70 J/cm$^2$) was performed on the entire face or back surface for a duration of 23 minutes (LumiPhase-R/B™, OPUSMED Inc. Montreal, Canada). No cooling method was used. Digital photographs (Canon Dual Flash EOS 10D, Canon, Tokyo, Japan with EX SIGMA 50 mm 1:2.8 macro lens, Sigma, Aizu, Japan) were taken prior to and four weeks after the procedure. Each photograph was taken maintaining identical ambient lighting, pose and camera angles.

Acne Lesion Counts:

Acne lesion counts were performed before and four weeks after the PDT treatment. All types of inflammatory (papules, pustules, nodules) and noninflammatory (open and closed comedones) acne lesions were counted. Lesion counts were performed based on the digital photographs by two non-treating physicians who were blinded to the treatment regimen (IR-treated or control side) and to the timing of the photographs (baseline or post-treatment).

Clinical Global Severity Assessment:

The global severity of acne was assessed at the end of the study by the three non-treating physicians, as described above, using a six-point rating scale (Table 1). Clinical success was defined by grades 0 (clear) or 1 (almost clear).

Adverse Effects:

Adverse reactions were monitored throughout the study. Signs of erythema, oedema, scaling/crusting, bronzing, textural changes, hyperpigmentation, and hypopigmentation were documented during the time period of the clinical trial.

Statistical Analysis:

In order to achieve an 80% chance of detecting (at the two sided 5% level), a 20% difference between the IR-treated and control sides in percent change from baseline in inflammatory lesions at week-4, with an assumed standard deviation of 15, nine patients were required. To account for a 90% per protocol completion rate, the planned number of patients to be enrolled was 10.

Cronbach's alpha was calculated to assess inter-rater reliability in assessments. Reliability was deemed acceptable if Cronbach alpha was ≥7 allowing raters' assessments to be combined for analysis. The primary outcome variable was the percent change from baseline in inflammatory lesion count measured four weeks post-treatment. Secondary efficacy variables included percent change from baseline in noninflammatory lesion and severity score at the end of the study. The Mann-Whitney test was used to compare the two treatment sides. The p-values were considered significant at p≤0.05. SPSS 16.0 statistical software was used.

Results

Figure 8:
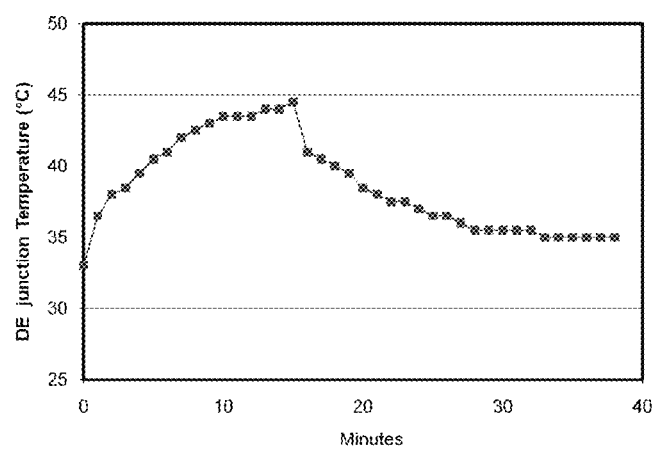
FIG. 8: Photopreparation by radiant infrared irradiation increases skin temperature. The temperature (° C.) increase with 970 nm light emitting diode at 80 mW/cm$^2$ was measured at the derma-epidermal (DE) junction as a function of time (minutes) for each patient. Data monitoring attested that the temperature peaked at 45° C. after 15 minutes of irradiation and decreased slowly thereafter. The data are from Patient #1.
Figure 9:
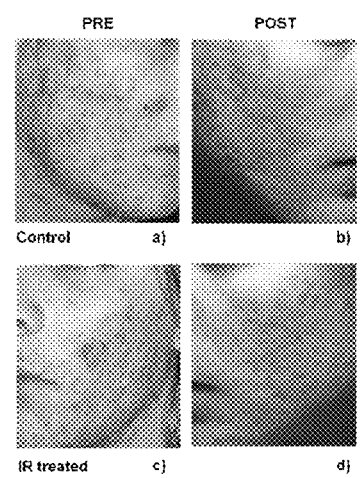
FIG. 9: Improved clinical outcome with infrared pre-treatment. Clinical photographs of a male patient aged 19 taken pre and four weeks post photodynamic therapy (PDT) for the control side (a-b) and infrared (IR) treated side (c-d). The photographs at the right show an increased therapeutic response on the IR-treated side (d) as opposed to the control side (b) post PDT treatment.

In the present study, skin temperature was increased on one side with radiant IR prior to ALA-PDT and compared to the contralateral side treated with ALA-PDT alone. Temperature variations were registered by thermocouple probes and were never greater than 45° C. (basal dermo-epidermal junction temperature of 33° C.±0.5° C.). Monitoring thus attested that skin temperature prior to ALA application reached the target temperature within 15 minutes (FIG. 8).

Patient characteristics and lesion types at baseline are presented in Table 2. One patient was lost to follow-up, and therefore nine patients were included in the analyses. At baseline, there was no difference in lesion counts between the two sides in all lesion types except for Papules (p=0.037). The inter-rater reliability in assessments was found to be high (Cronbach's α 0.8 to 0.9); data from the different raters was thus combined for analysis.

The percent change from baseline in lesion counts post-treatment are presented in Table 3. The assessment of inflammatory acne at week-4 revealed a statistically significant reduction in lesion count on the IR-treated side (median 73%, 95% confidence interval (CI) 51-81%), in comparison to the control side (median 38%, 95% CI 8-55%) (p<0.0001). The IR-treated side thus produced an additional benefit of 35%. For the secondary efficacy variable of noninflammatory lesions, the percent change from baseline for the IR-treated side was found to be statistically superior to that of the control side (p=0.037). The results from the Clinical Global Severity Assessment also revealed a significant improvement on the IR-treated versus the control side (p=0.027) (Table 4). The clinical success rate (i.e. almost clear or clear categories of the Clinical Global Severity Assessment) was found to be higher on the IR-treated side than on the control side at week-4 (78% vs. 44%). FIG. 4 depicts before and after photographs of the IR-treated and control sides for a typical male patient.

The treatment was overall well tolerated with the majority of patients reporting a slight but bearable sensation of heat during photoactivation. Most patients presented with slight erythema post-PDT which disappeared within 48 hours, and two patients experienced acneiform folliculitis for 3-4 days. Aside from slight erythema and mild crusting, no other adverse signs, such as post-inflammatory hyperpigmentation (PIH), were observed in patients.

Discussion

Conventional treatments such as topical and systemic antibiotics and isotretinoin may be a good treatment option for patients with acne vulgaris. However, many such patients exhibit transient effects and severe adverse reactions, and therefore need other treatment options. As an alternative, topical ALA-PDT treatment has been used with appreciable results. The efficacy of ALA-PDT in the treatment of acne was first described using very high fluence (up to 200 Joules/cm$^2$). Thus far, however, anti-acne ALA-PDT effects have only been documented in a limited number of randomized controlled clinical trials.

The rationale for the use of ALA-PDT against acne is based on the ability of ALA to penetrate sebaceous glands, reach *P. acnes* and increase PpIX synthesis. ALA-PDT efficacy is limited by the ability of ALA to penetrate the skin and induce PpIX accumulation. In the present study, we investigated the impact of pre-treating skin by increasing skin temperature by means of radiant IR radiation to circumvent these limitations to enhance clinical outcomes of patients with inflammatory type acne. The results from the present study revealed that, when skin was pre-heated with IR radiation, significant additional benefits over the non heated side were observed for inflammatory and noninflammatory lesions, as well as in acne global severity scores four weeks post-treatment. The improvement seen on the ALA-PDT control side was in the range of previous accounts of the effectiveness of LED and other PDT light sources in the treatment of acne.

IR radiation typically induces molecular vibrations and rotations and by so doing increases skin temperature [xxix]. Given the considerable depth of penetration at 970 nm, this photopreparation method provides an inside-out heating, up to the reticular dermis where the targeted sebaceous glands are located. Although the mechanisms at play have not been investigated in the present study, the observed temperature-related additional therapeutic benefits may be due to the induction of alterations in transcutaneous diffusion kinetics of the photosensitizer allowing enhanced percutaneous penetration of ALA and subsequent PpIX formation. There is also the possibility that part of the effect might be related to enhanced conversion of ALA to PpIX due to the elevated skin temperature during incubation. Indeed, temperature monitoring revealed that skin temperature remained above physiological level during the major part of the incubation period.

The observed therapeutic effects were seen after only one PDT treatment with red light (630 nm). Red light penetrates deep into tissues, reaching the targeted sebaceous glands [xxx]. The mechanism of action is thought to involve the ALA-induced increase in endogenous PpIX synthesis, which absorbs light during photoactivation to form singlet oxygen and reactive radicals, leading to eradication of *P. acnes* and destruction of the pilosebaceous unit. In addition, red light may also have anti-inflammatory properties by influencing cytokine release from macrophages that stimulate fibroblast proliferation and the production of growth factors, thereby influencing the process of inflammation, healing, and wound repair [xxxi, xxxii].

The results from this study also showed that the performed therapy was well tolerated with no significant adverse events, likely due to the low level characteristics of LED. Other PDT light sources, such as Intense Pulsed Light and Pulsed Dye Lasers, are often associated with important side effects such as severe swellings and erythema after treatment which, although transient, can be inconvenient and lead to patient withdrawal. From a clinical perspective, the absence of thermal injury (peak power effects) to the skin during light activation may yield a significant advantage over other light-based methods, given that improvements can be achieved without thermal damage and with limited adverse reactions. Hence, one must not underestimate the importance of dose-rate during PDT when using low level light sources such as LEDs to progressively photoactivate the photosensitizer with the appropriate wavelength capable of reaching the sebaceous glands in the red spectrum [xxxiii].

Near IR irradiation to prepare skin for ALA-PDT treatment of acne patients appears to be a clinically significant method. Although pre-heating of skin prior to ALA application adds fifteen minutes to the total procedure time, the additional clinical benefits seen with this innovative method outweigh the additional time. IR pre-treatment with ALA-PDT was shown to produce notable results with limited side effects after only one treatment, thereby limiting concerns over patient compliance. Moreover, it is very easy to perform in a clinical setting, and less invasive than other pre-treatment modalities (e.g., micro-dermabrasion) [xxxiv]. The use of IR-PDT in acne might prove to reduce the need for long-term conventional treatments, such as antibiotic use associated with the growing potential of inducing antibiotic-resistant bacteria and retinoid systemic side effects. This procedure might also be useful in the treatment of other skin conditions where PDT has been found to be helpful, such as superficial basal cell carcinoma and Bowen disease [xxxv, xxxvi].

TABLE 1

Clinical Global Severity Assessment

| Grade | Severity | Description |
|---|---|---|
| 0 | Clear | Residual hyperpigmentation and erythema may be present |
| 1 | Almost clear | A few scattered comedones and a few (less than five) small papules |
| 2 | Mild | Easily recognizable; less than half the area is involved. Many comedones and many papules and pustules |
| 3 | Moderate | More than half of the area is involved. Numerous comedones, papules and pustules |
| 4 | Severe | Entire area is involved. Covered with comedones, numerous papules and pustules and few nodules and cysts |
| 5 | Very Severe | Highly inflammatory acne covering the area; with nodules and cysts present |

TABLE 2

Patient Characteristics and Lesion Types at Baseline

| Patient Characteristics | | | |
|---|---|---|---|
| % Male | 70% | | |
| Age [years, mean (range)] | 26.2 (13-54) | | |
| Fitzpatrick skin Type | | | |
| % Type I | 20% | | |
| % Type II | 40% | | |
| % Type III | 40% | | |
| Global severity score | | | |
| Mild | 50% | | |
| Moderate | 50% | | |
| Treated area | | | |
| Face | 80% | | |
| Back | 20% | | |
| Lesion Type | Median (SD) | Min | Max |
| IR-Treated side | | | |
| Papules | 12 (26) | 5 | 90 |
| Pustules | 4 (11) | 0 | 64 |
| Nodulo-cystic lesions | 3 (3) | 0 | 9 |
| Open comedones | 0 (4) | 0 | 12 |
| Closed comedones | 0 (1) | 0 | 4 |
| Control side | | | |
| Papules | 6 (13) | 3 | 45 |
| Pustules | 2 (11) | 0 | 33 |
| Nodulo-cystic lesions | 2 (2) | 0 | 7 |
| Open comedones | 0 (2) | 0 | 6 |
| Closed comedones | 0 (1) | 0 | 4 |

TABLE 3

Change from Baseline in Lesion Counts

| Type of lesions | Treatment side | Median | SD | 95% Confidence Interval for Mean | | Min | Max |
| --- | --- | --- | --- | --- | --- | --- | --- |
| | | | | Lower Bound | Upper Bound | | |
| Papules | IR-Treated | 75.00% | 35.61% | 33.30% | 88.04% | −29.00% | 82.00% |
| | Control | 38.10% | 40.05% | −9.68% | 51.90% | −50.00% | 69.00% |
| Pustules | IR-Treated | 37.65% | 28.00% | 10.81% | 53.86% | 0.00% | 70.00% |
| | Control | 0.00% | 34.42% | 3.43% | 56.35% | 0.00% | 89.00% |
| Nodules | IR-Treated | 100.00% | 42.54% | 41.19% | 106.59% | 0.00% | 100.00% |
| | Control | 20.00% | 40.50% | 7.54% | 69.80% | 0.00% | 100.00% |
| Total Inflammatory lesions | IR-Treated | 73.21% | 19.45% | 50.61% | 80.51% | 23.00% | 85.00% |
| | Control | 37.86% | 30.40% | 8.30% | 55.03% | −27.00% | 72.00% |
| Open comedones | IR-Treated | 0.00% | 32.09% | −8.55% | 40.78% | 0.00% | 78.00% |
| | Control | 0.00% | 55.40% | −62.03% | 23.14% | −167.00% | 0.00% |
| Closed comedones | IR-Treated | 0.00% | 33.33% | −14.51% | 36.73% | 0.00% | 100.00% |
| | Control | 0.00% | 33.33% | −14.51% | 36.73% | 0.00% | 100.00% |
| Total Noninflammatory lesions | IR-Treated | 0.00% | 41.69% | −4.82% | 59.27% | 0.00% | 100.00% |
| | Control | 0.00% | 7.80% | −9.44% | 2.55% | −23.00% | 0.00% |

TABLE 4

Clinical Global Severity Assessment at Week-4

| Treatment side | Median | SD | 95% Confidence Interval for Mean | | Min | Max |
| --- | --- | --- | --- | --- | --- | --- |
| | | | Lower Bound | Upper Bound | | |
| IR-Treated | 1 | 0.76 | 0.74 | 1.34 | 0 | 3 |
| Control | 2 | 0.70 | 1.17 | 1.72 | 0 | 2 |

Example 10: Photopreparation Using Pulsed Light and Comparison with CW

Topical therapies are widely used in dermatology practice for different purposes. Their therapeutic efficacy is dependent & limited by drug permeability through the stratum corneum and diffusion through the dermis to reach the targeted structures. To overcome these limitations, photopreparation may prove to be a useful approach. Photopreparation is defined as the use of LLLT in the visible to infrared range as a mean to prepare the skin tissues to receive topical agents to optimize their intended therapeutic effects.

Photopreparation's underlying mechanism is thought to be dual. The first suggested mechanism is the induction of skin natural protection and repair mechanisms. The second proposed mechanism is skin temperature increase via impact on transcutaneous diffusion kinetics. Photopreparation may lead to enhanced delivery of topical agents through the skin layers, resulting in increased drug effects. Photopreparation appears to be a sound and promising approach with clinical implications for a number of dermatological procedures where topical agents are used, including Photodynamic Therapy (PDT) and anti-aging treatments.

Figure 10:
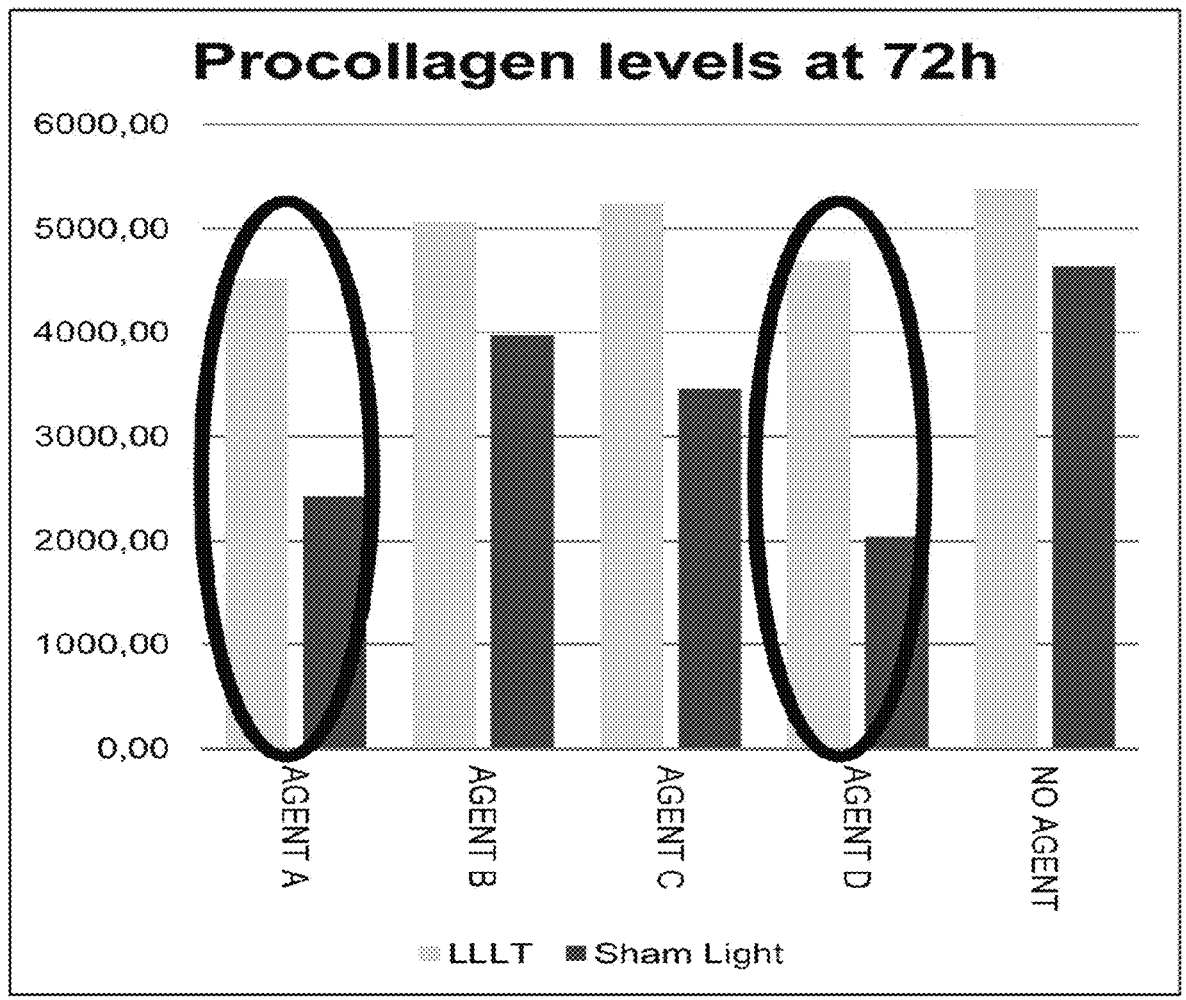
FIG. 10, in a bar chart, illustrates the results of an in vitro study of fibroblasts regarding collagen production in photopreparation.
Figure 11:
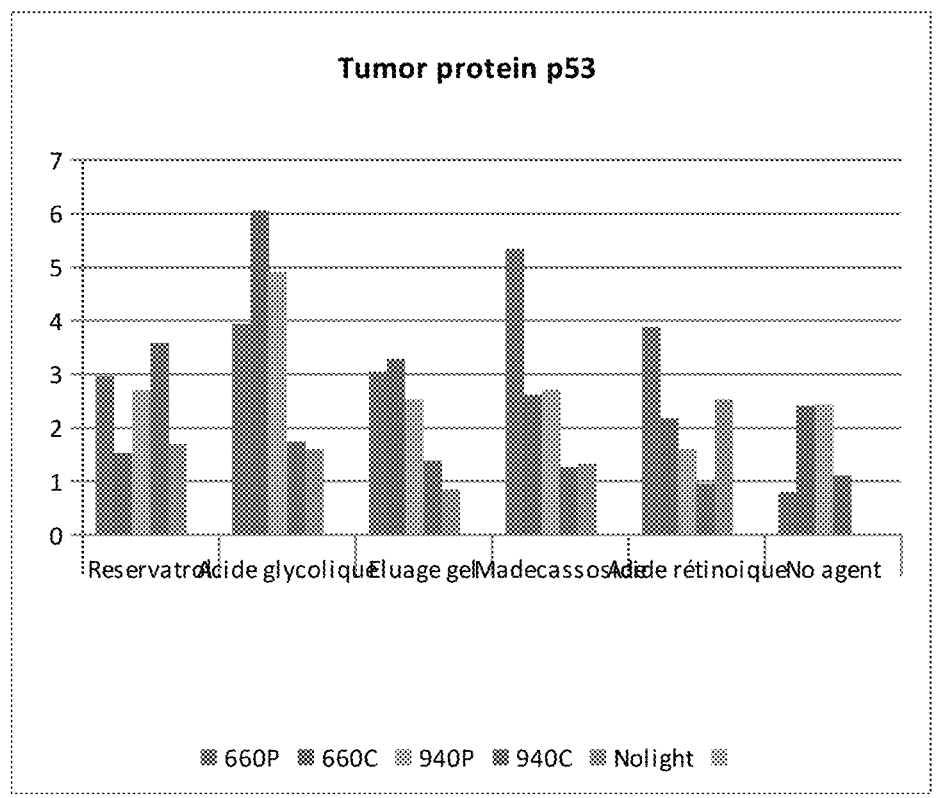
FIGS. 11 to 24, in bar charts, illustrate the PCR results in different conditions for a porcine study of photopreparation parameters for the application of light 15 mins prior to application of the agent, the legend being presented in the same order as the bars within each bar group in the graph.
Figure 12:
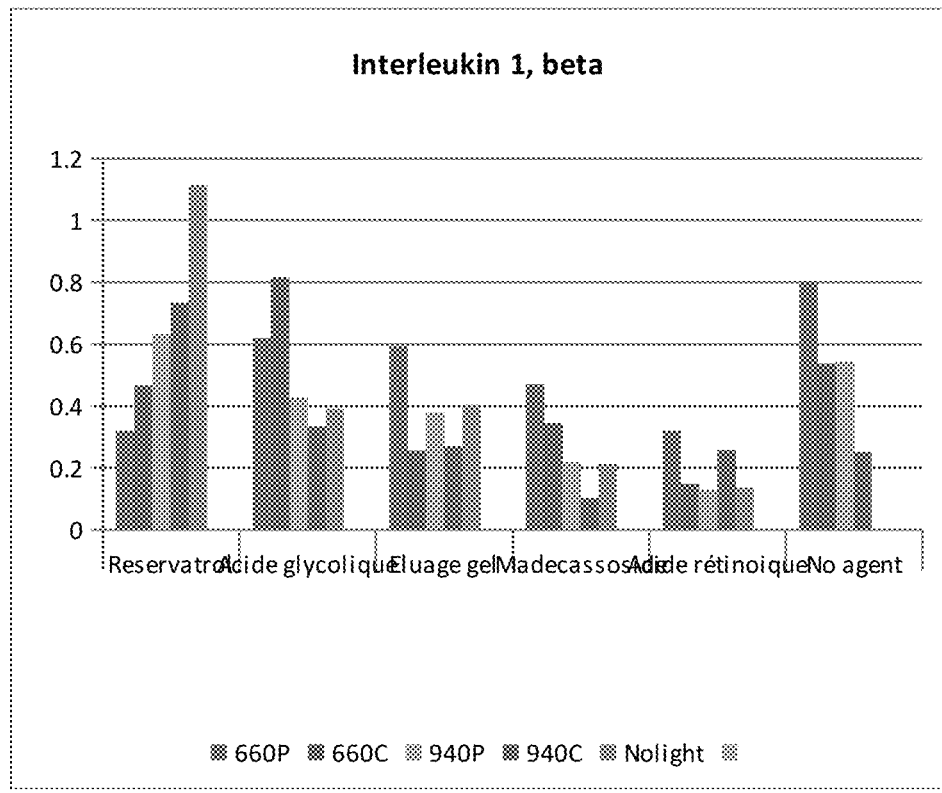
Figure 13:
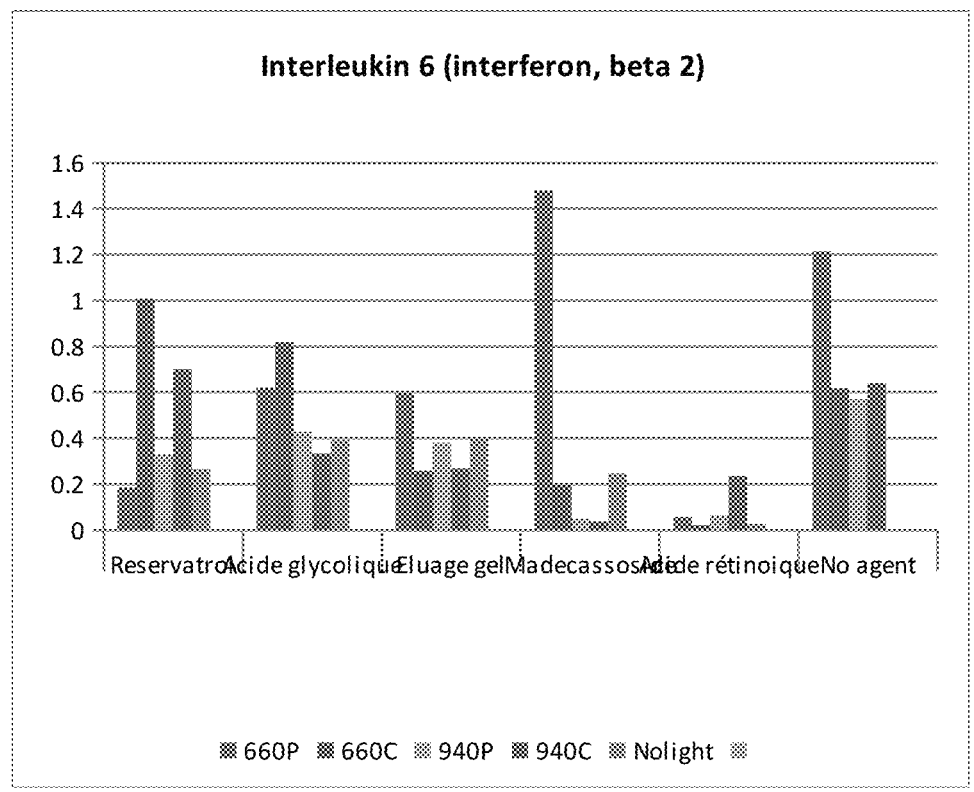
Figure 14:
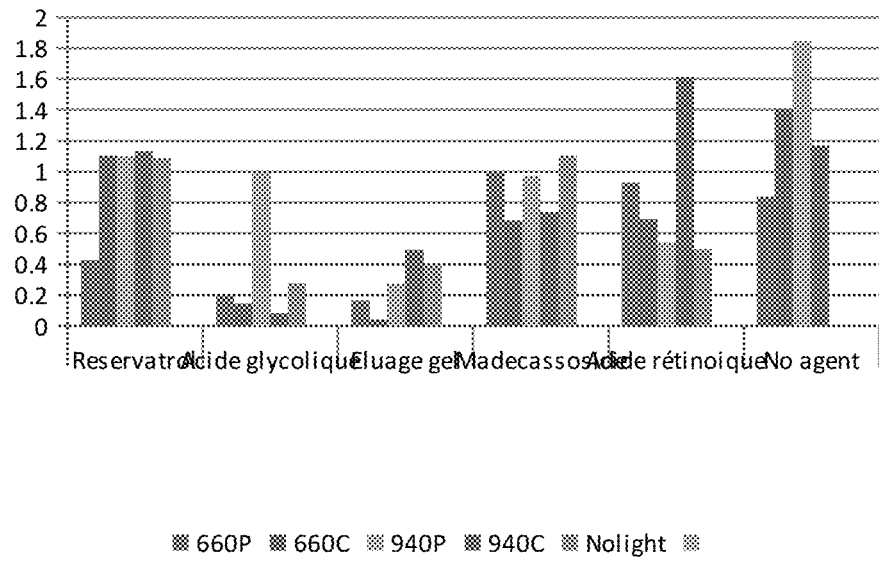
Figure 15:
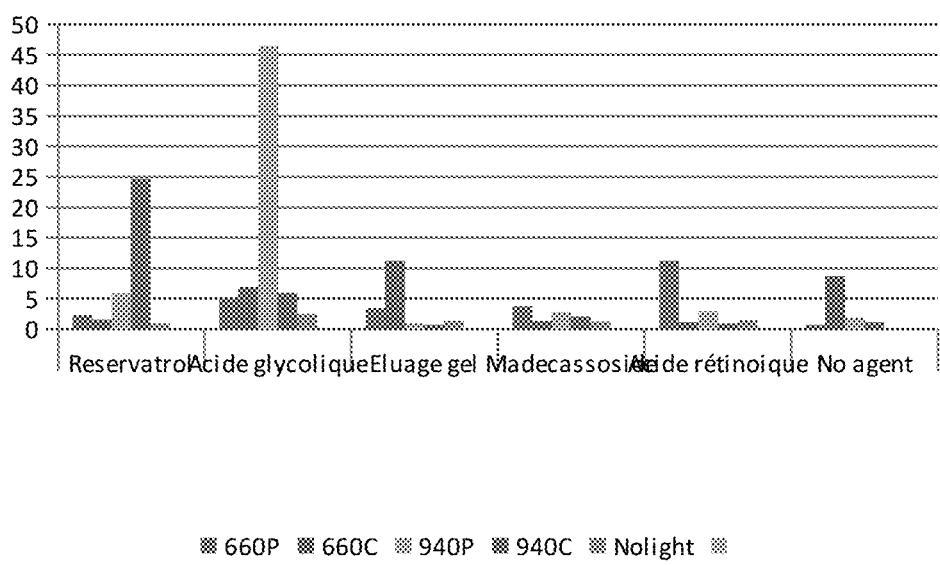
Figure 16:
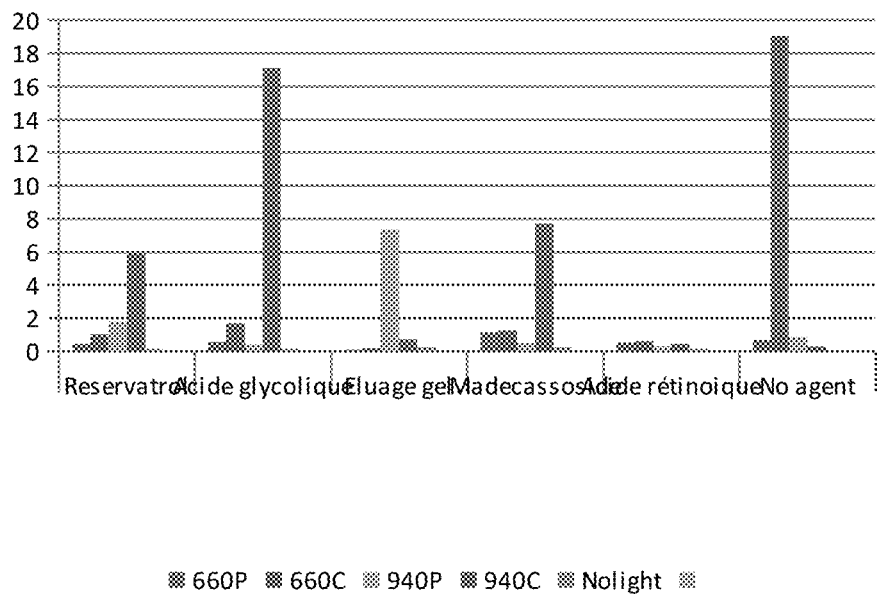
Figure 17:
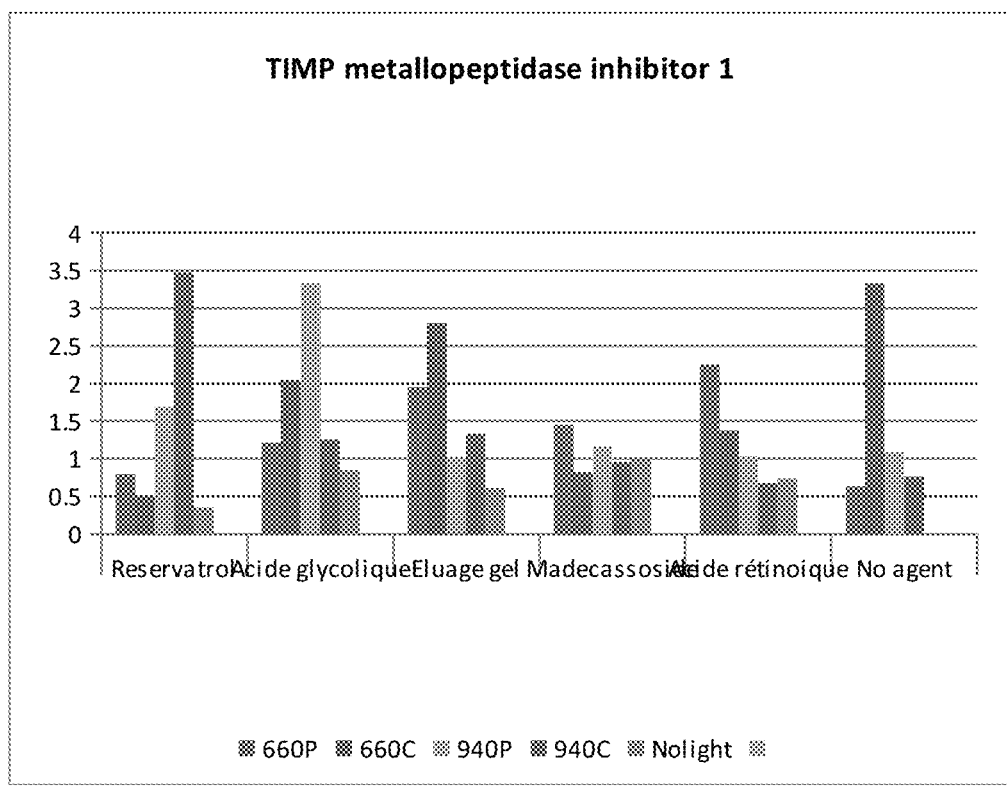
Figure 18:
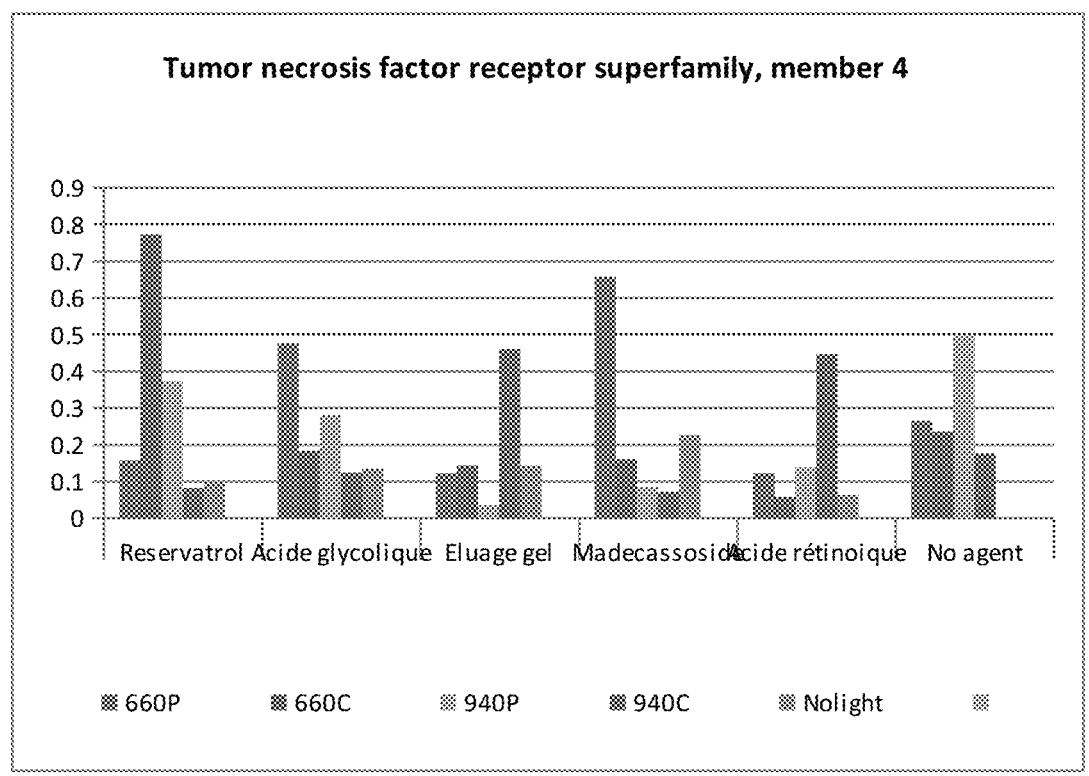
Figure 19:
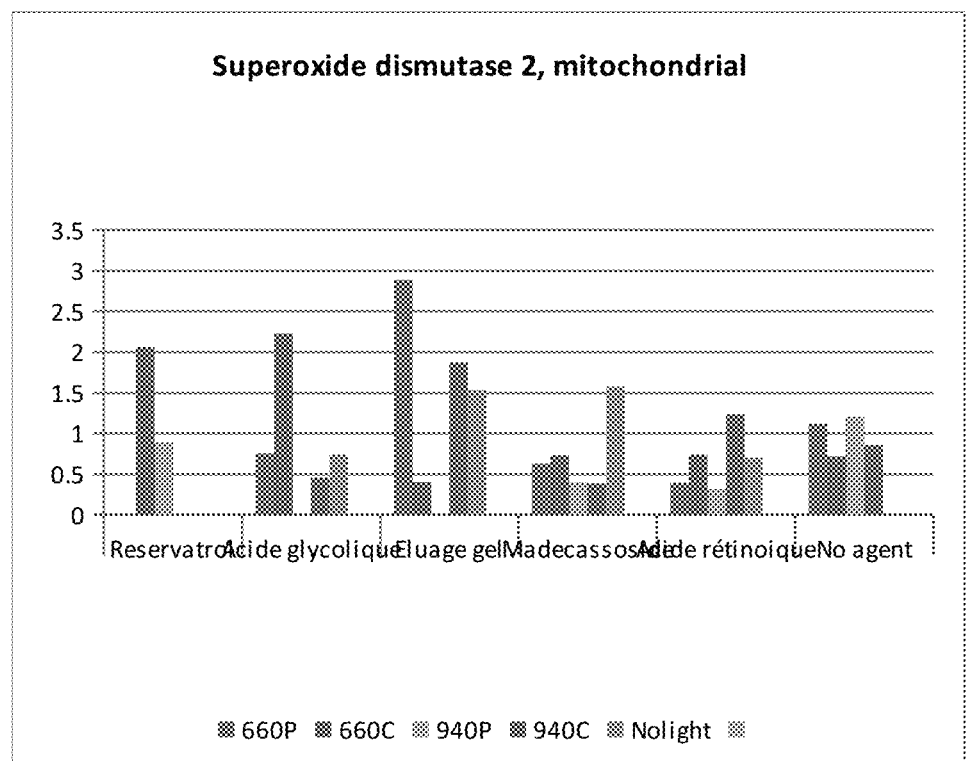
Figure 20:
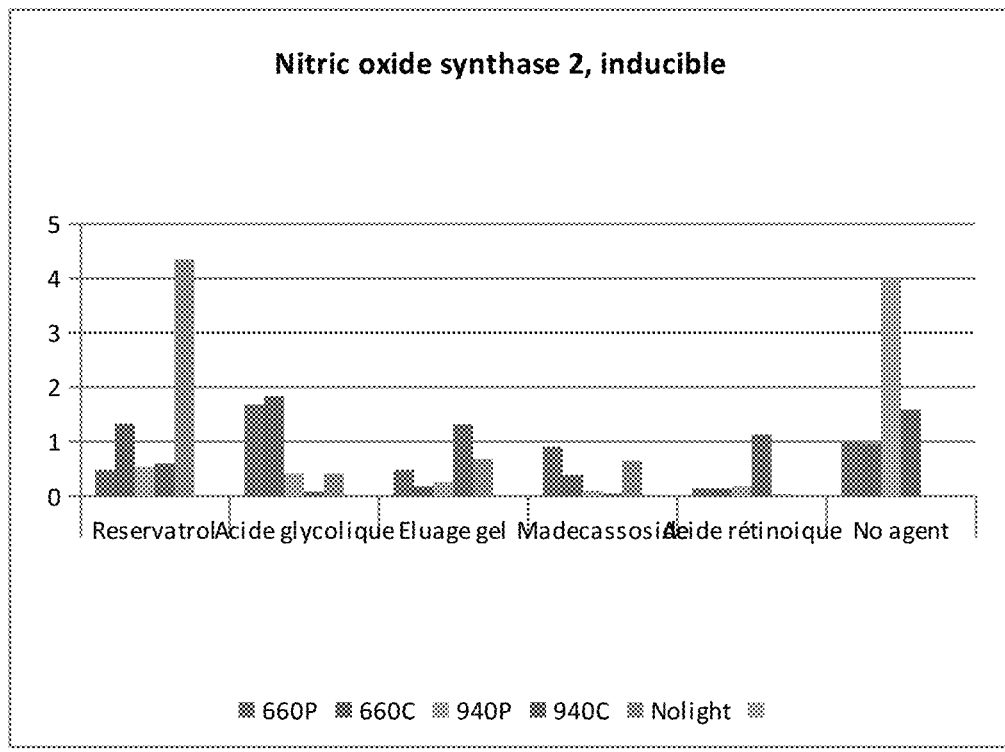
Figure 21:
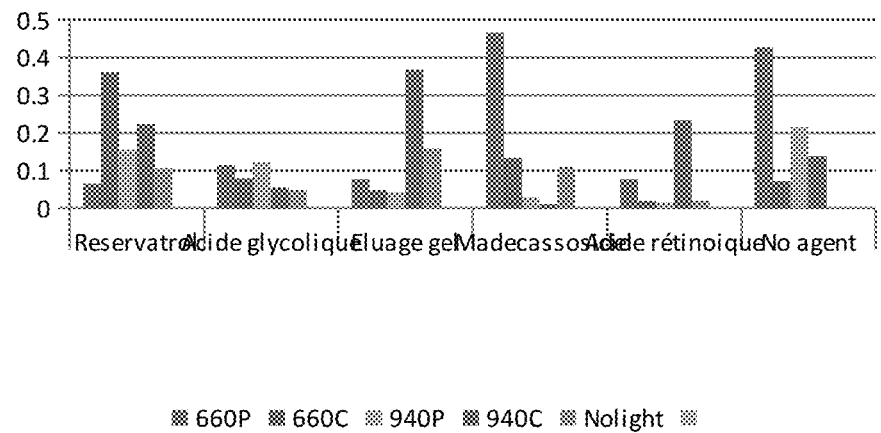
Figure 22:
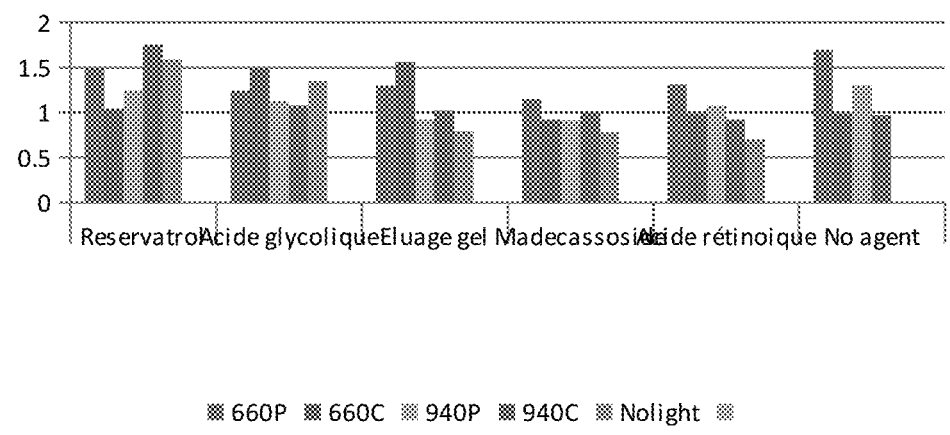
Figure 23:
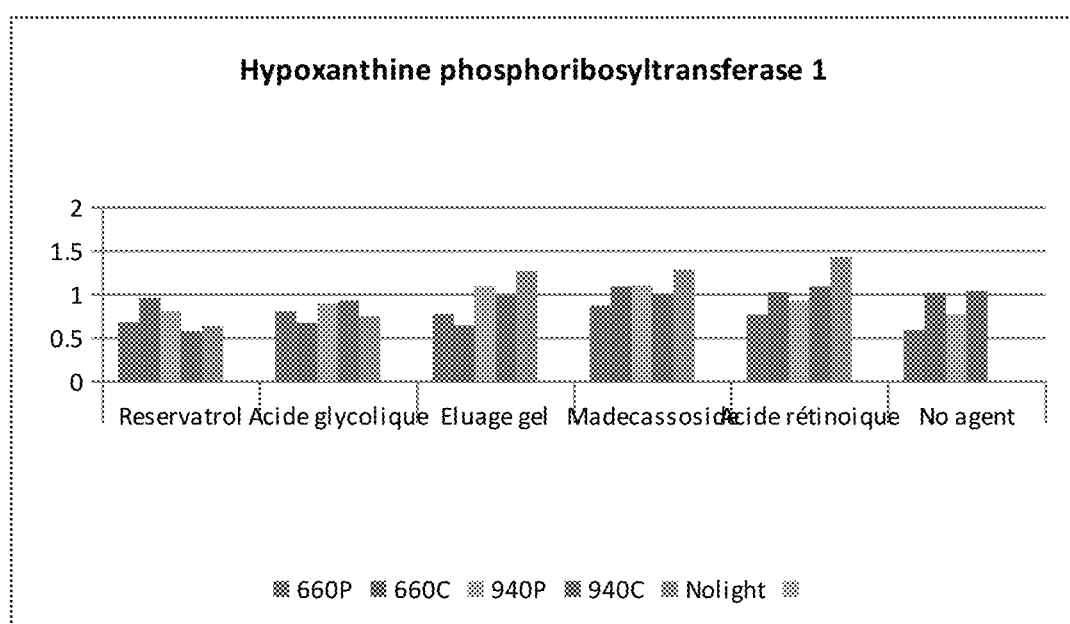
Figure 24:
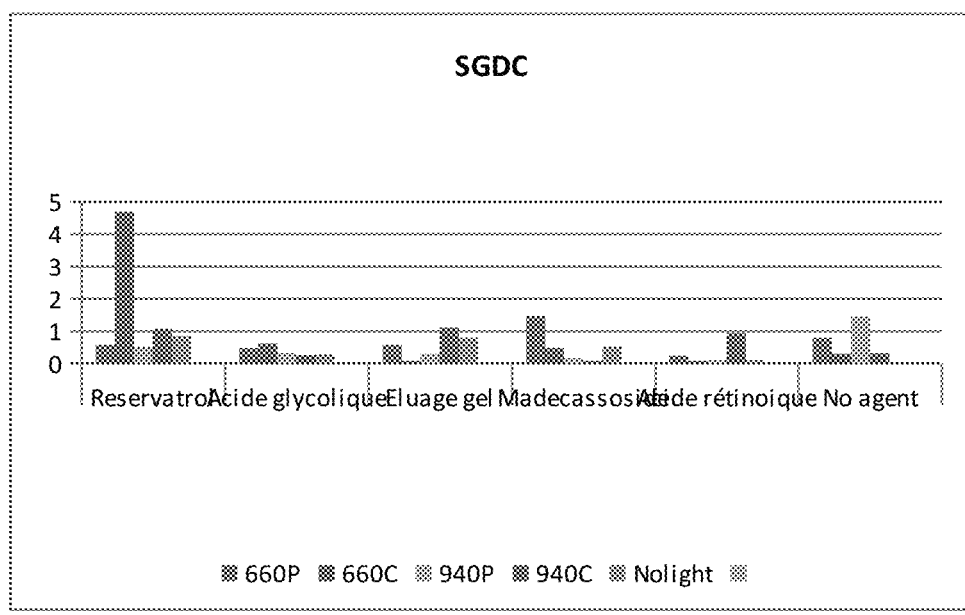
Figure 25:
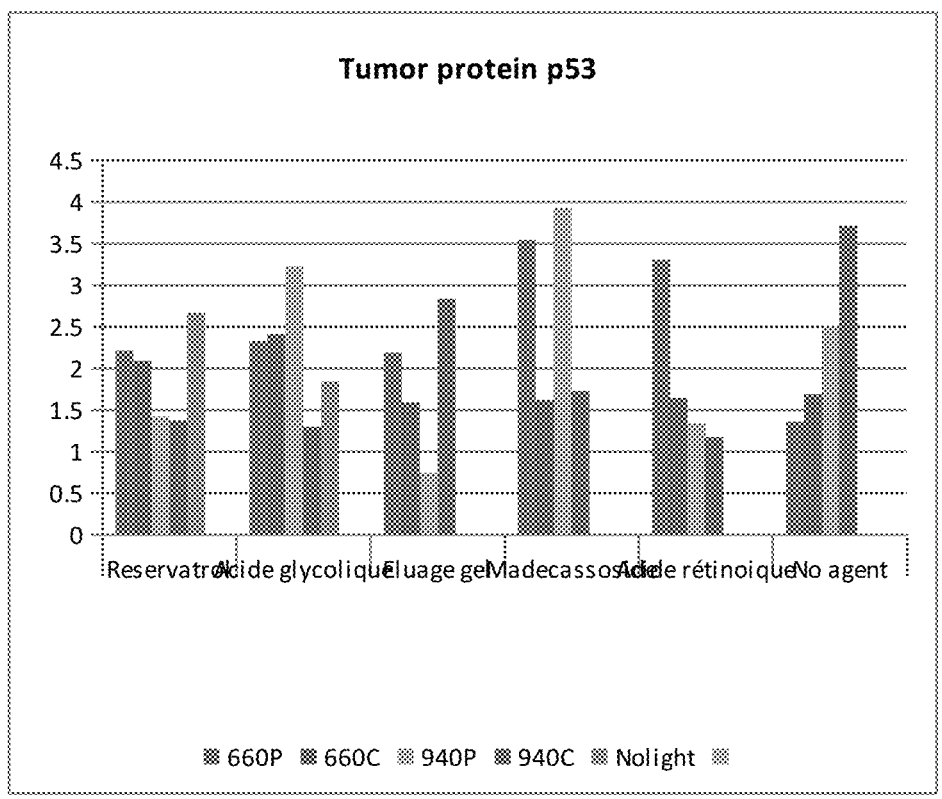
FIGS. 25 to 38, in bar charts, illustrate the PCR results in different conditions for the protocol relating to FIGS. 11 to 24 for the application of light 15 mins after application of the agent, the legend being presented in the same order as the bars within each bar group in the graph.
Figure 26:
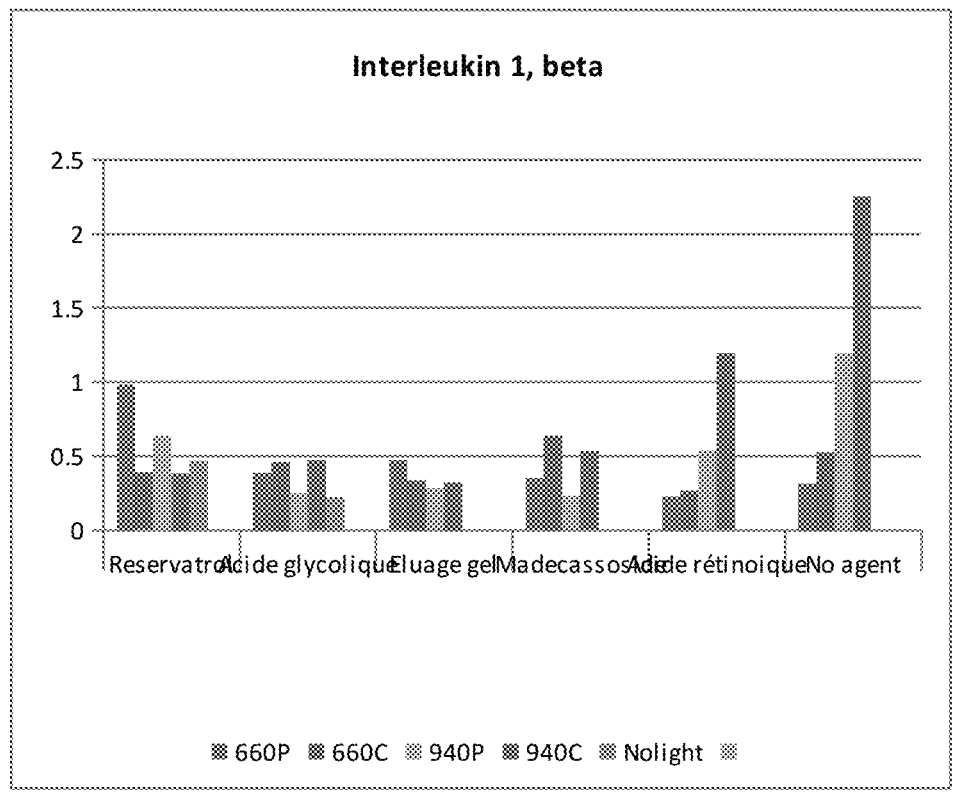
Figure 27:
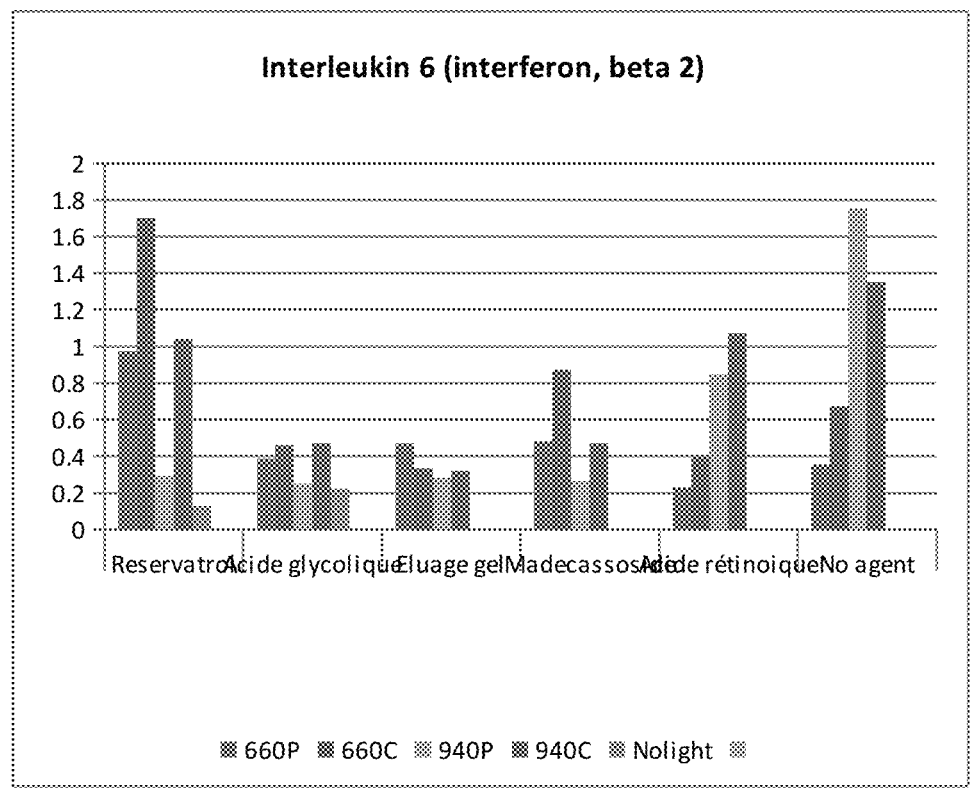
Figure 28:
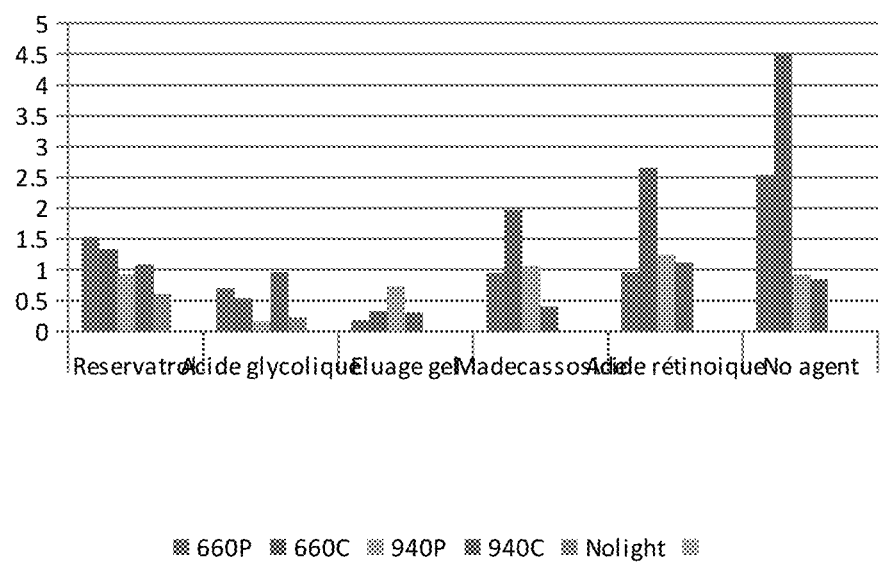
Figure 29:
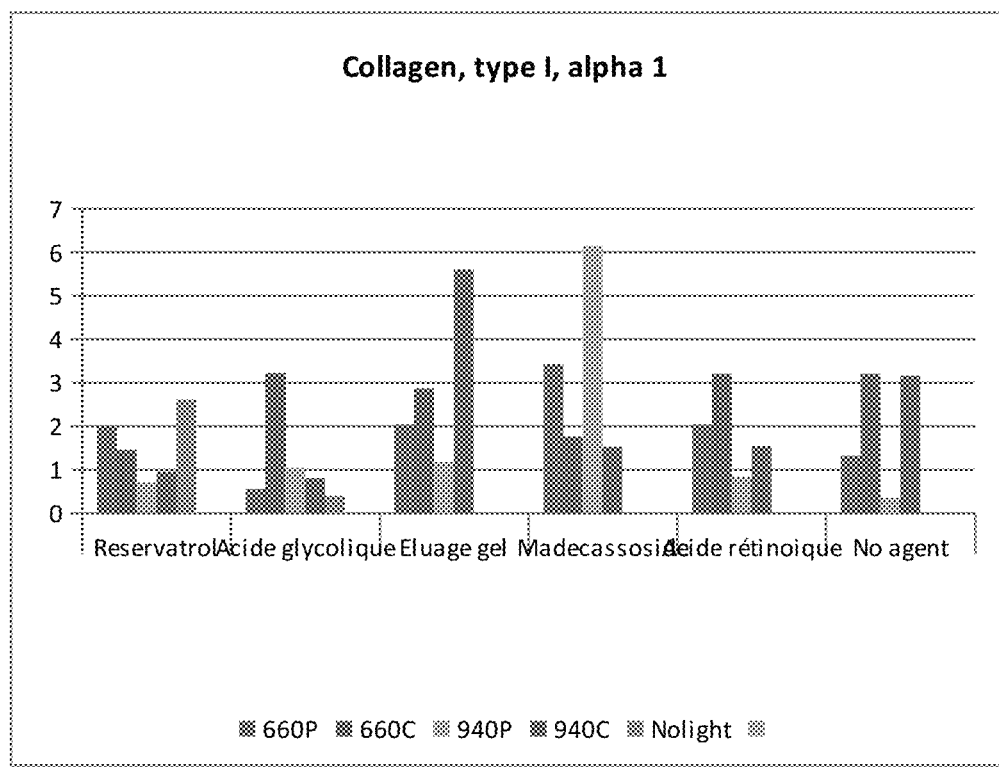
Figure 30:
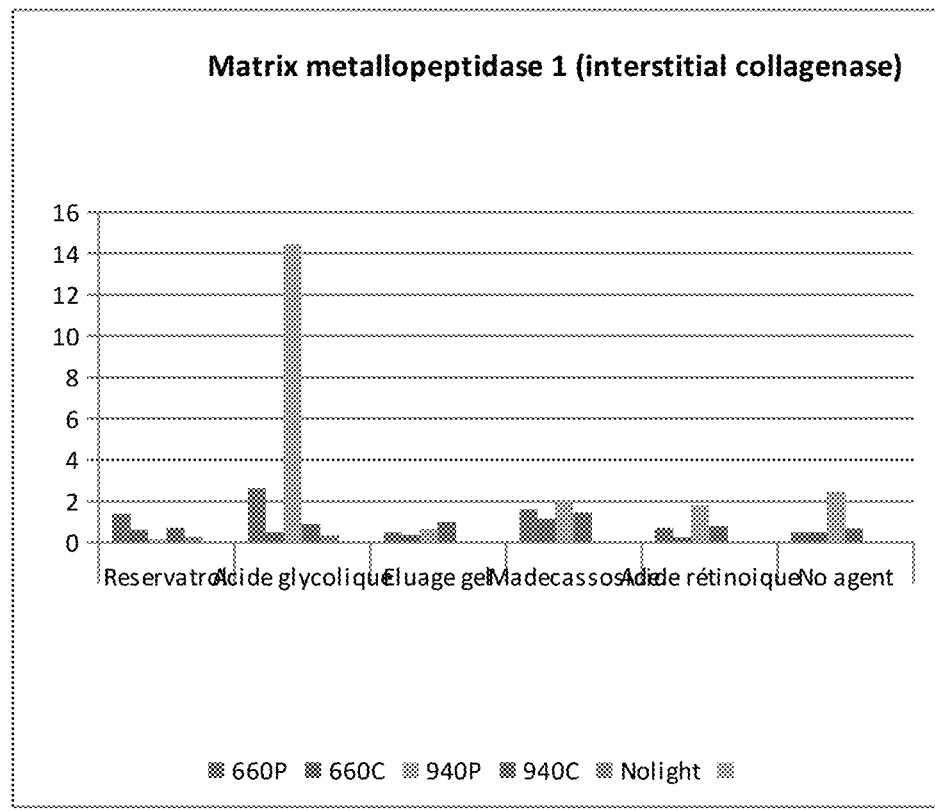
Figure 31:
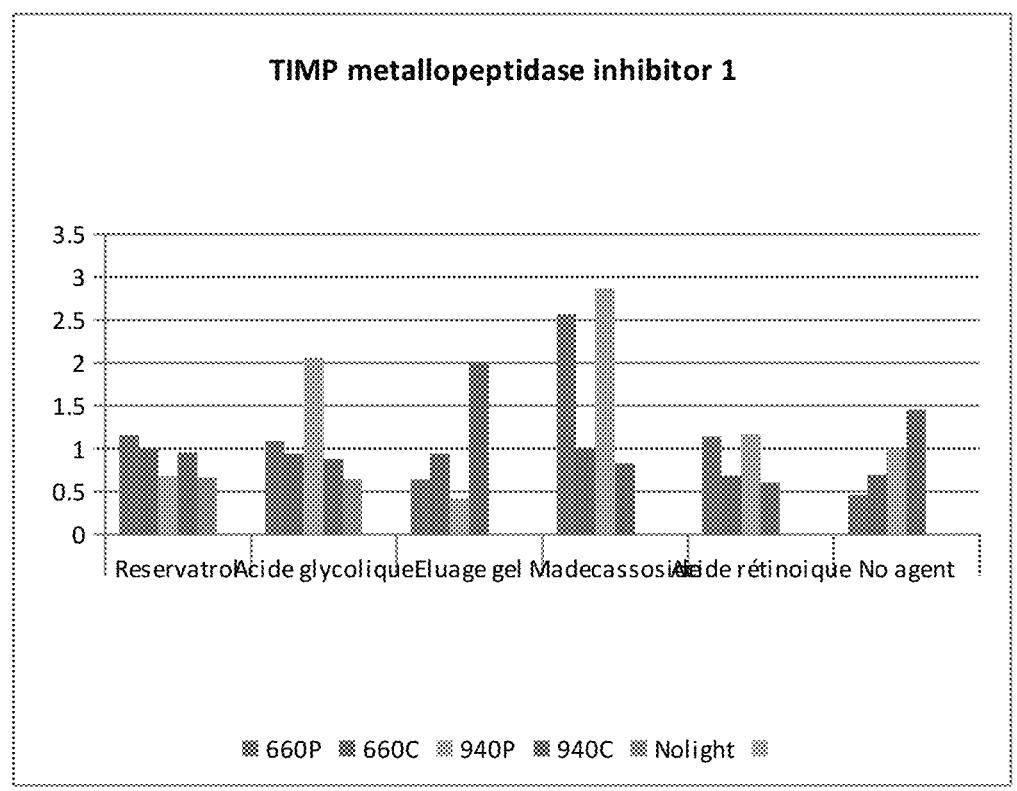
Figure 32:
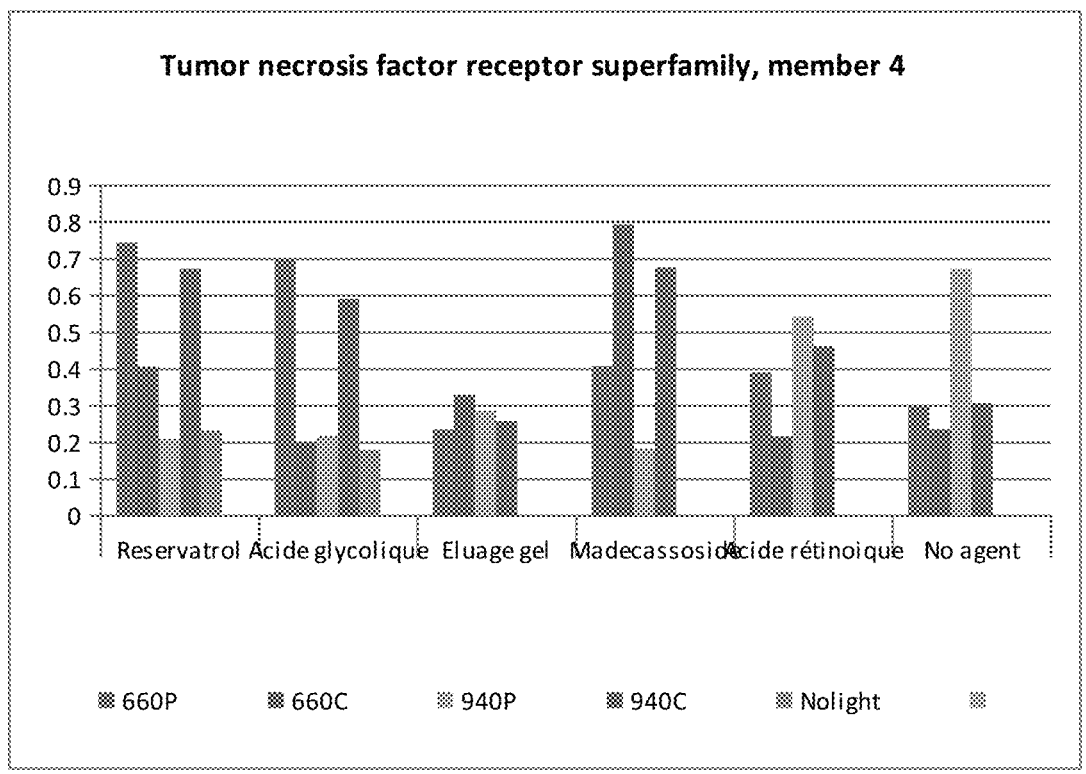
Figure 33:
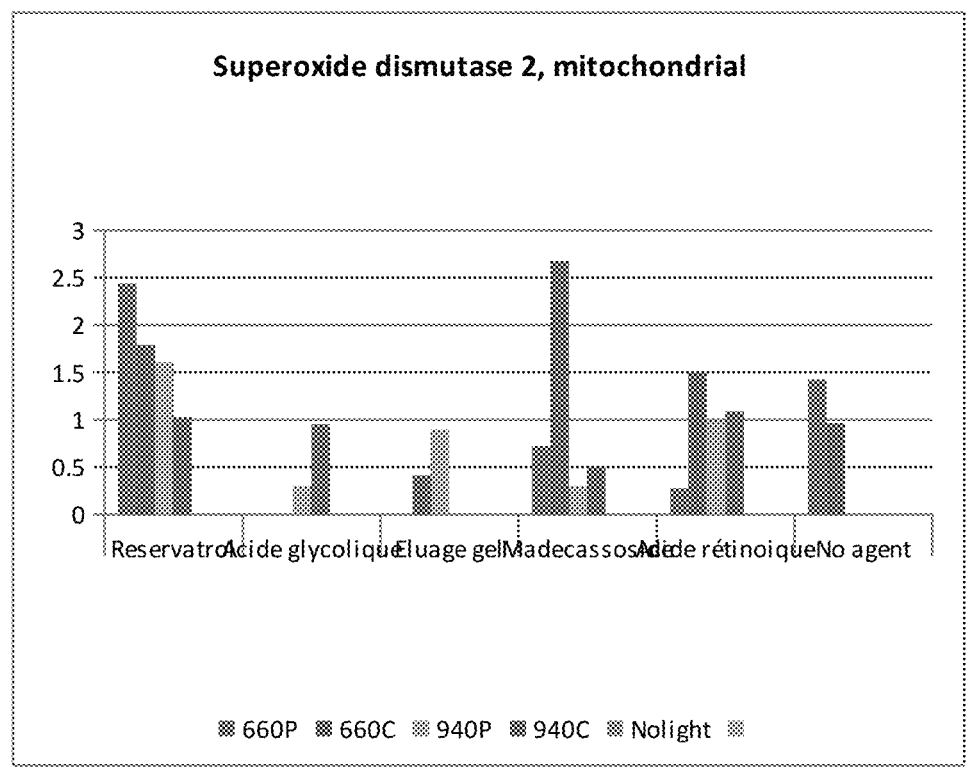
Figure 34:
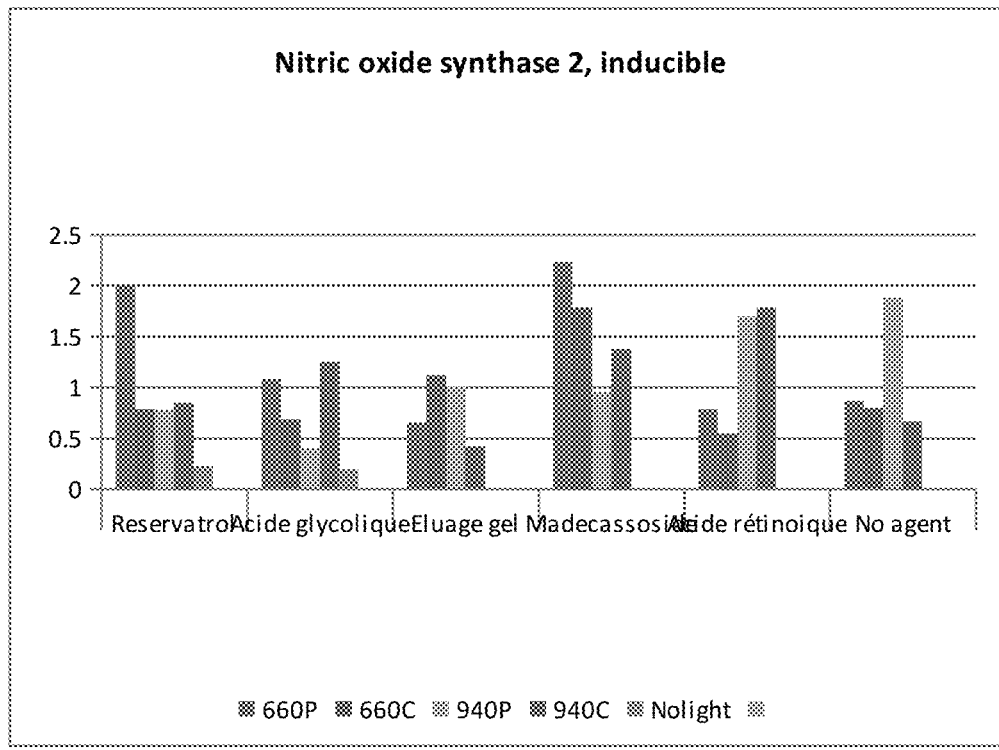
Figure 35:
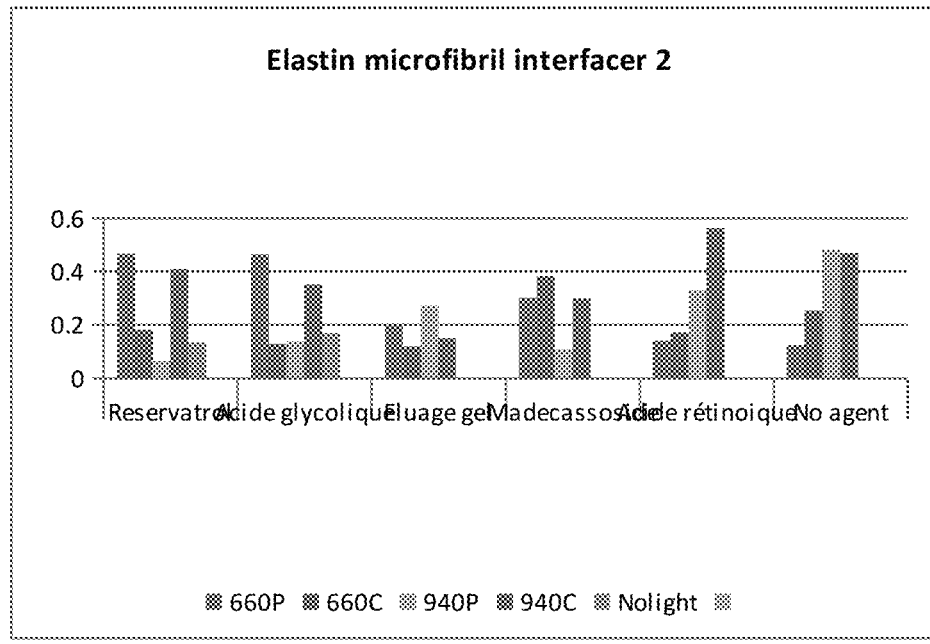
Figure 36:
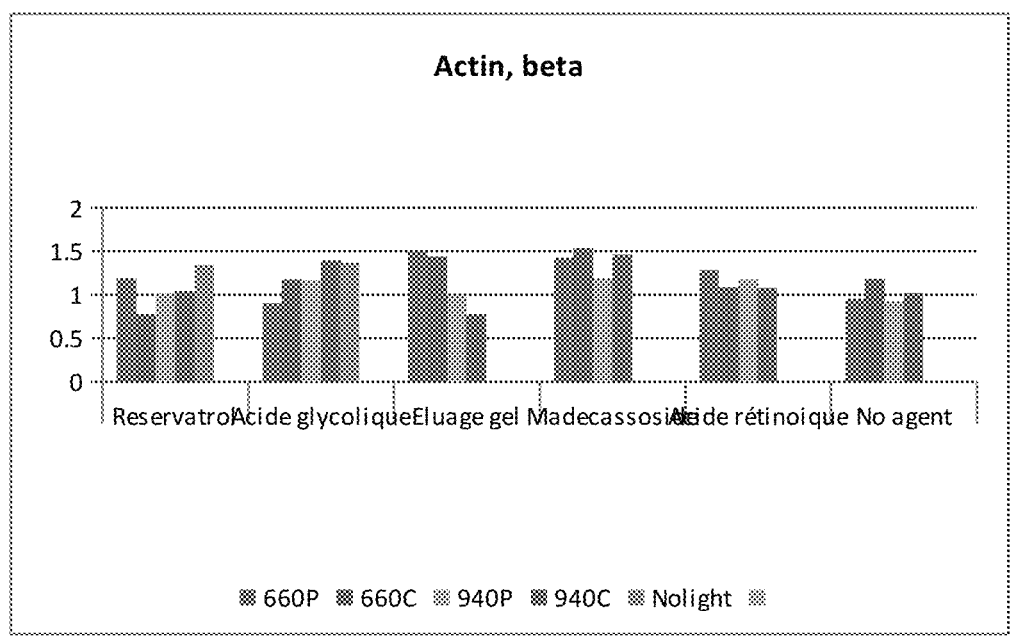
Figure 37:
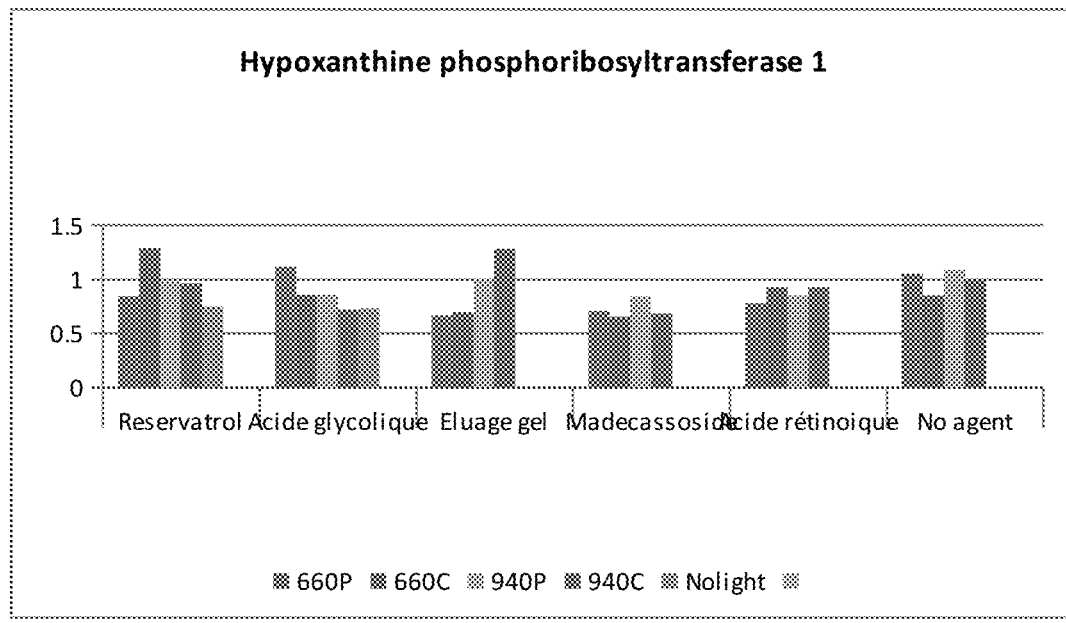
Figure 38:
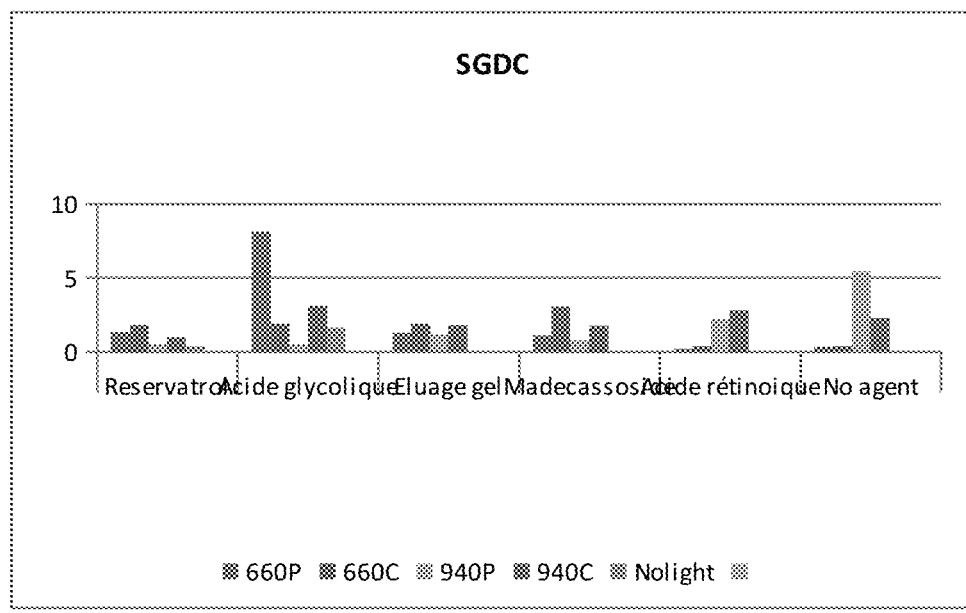
Figure 39:
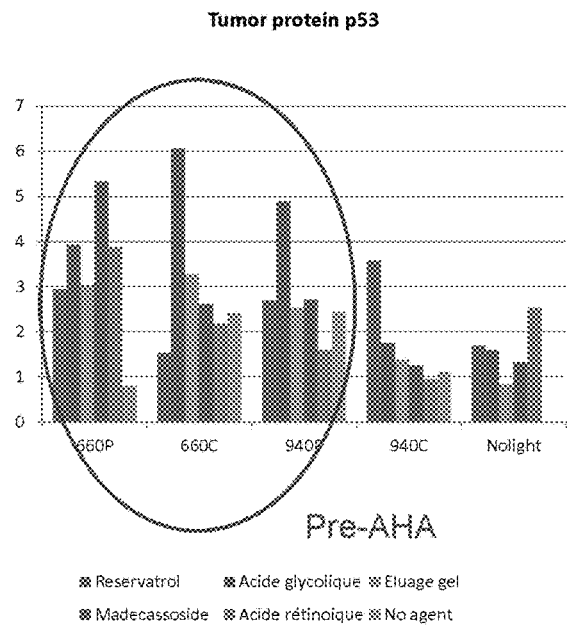
FIGS. 39 and 40, in bar charts, illustrates the effect of treatment on p53 from the data of FIGS. 11 to 38, the legend being presented in the same order as the bars within each bar group in the graph.
Figure 40:
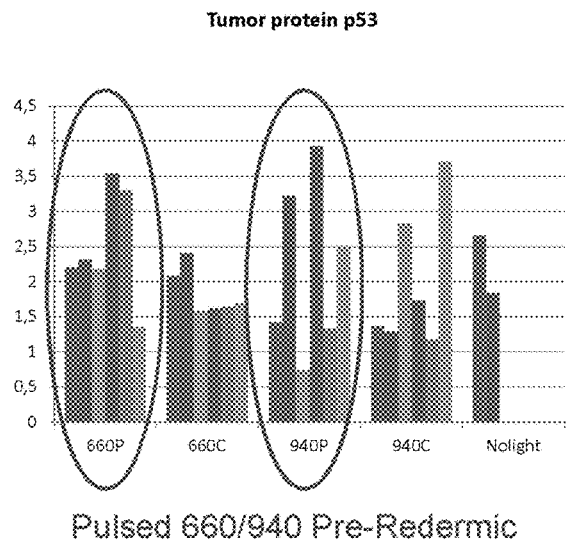
Figure 41:
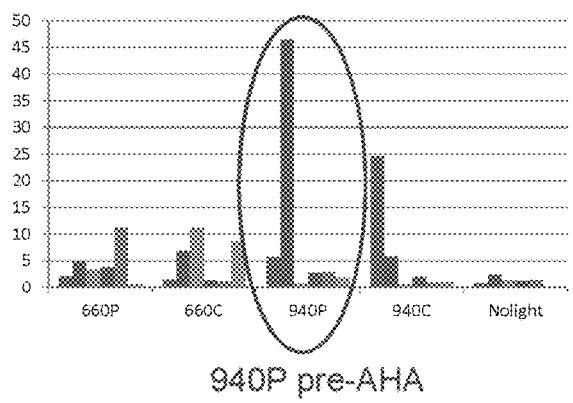
FIGS. 41 and 42, in bar charts, illustrates the effect of treatment on Collagen 1 from the data of FIGS. 11 to 38, the legend being presented in the same order as the bars within each bar group in the graph.
Figure 42:
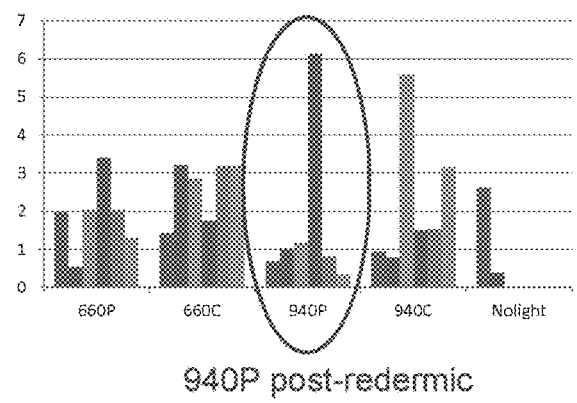
Figure 43:
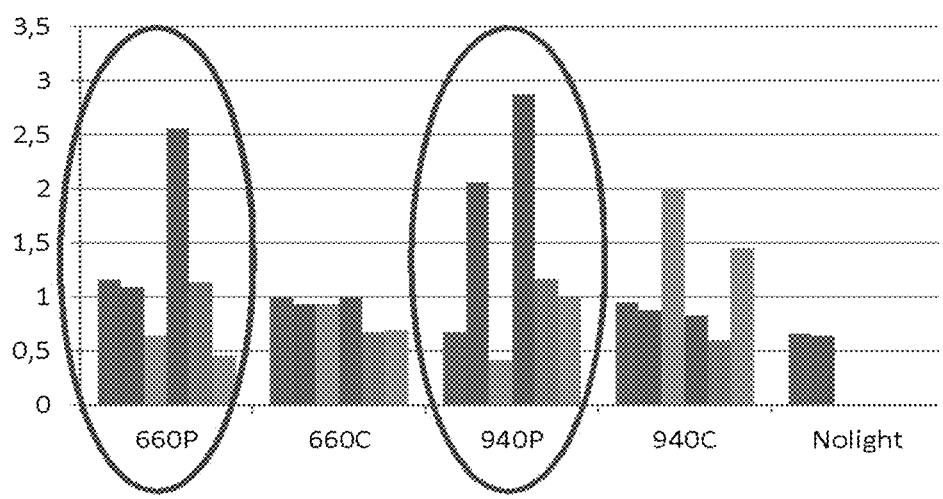
FIG. 43 is a rearrangement of the data shown in FIGS. 11 to 38, the legend being presented in the same order as the bars within each bar group in the graph.

In an in vitro study in fibroblasts, human primary fibroblast were cultured in monolayers and pre-treated with 810, 870, 940 nm LED light or sham light at an irradiance of 10 mW/cm2 for a fluence of 4 J/cm2. Active topical agents or no agent was applied 15 minutes after illumination Type-1 procollagen levels were assessed (ELISA) 72 h post-IR. Steps were repeated at 24 h intervals up to 72 h. Results are shown in FIG. 10.

LLLT can significantly augment Type-1 procollagen production and that a LLLT/Agent combination can increase production of collagen vs LLLT alone. However, the wavelength, illumination mode, timing of LLLT and the cumulative effects of LLLT are unknown. To study these latter parameters, experiments were performed with the primary objective of assessing the efficacy and safety of LLLT in combination with active topical agents to enhance collagen production. Secondary objectives included assessment of the impact of treatment parameters: Wavelength: NIR vs. Red Spectrum→660 nm vs. 940 nm Illumination mode: Pulsed vs. CW→pulsed vs. CW Timing of LLLT exposure→pre vs. post topical agent Cumulative effect of LLLT→Acute vs. long-term effect.

In another experiment, adult Yorkshire pigs were used in an in vivo porcine model. LED illumination with 660 nm vs. 940 nm pulsed and CW vs. Control was studied. LLLT was performed 15 min prior or after agent application 2 times a week for 12 wks. Assessments were made 24 h post-treatment and every 4 weeks for up to 12 weeks. Outcomes were % change in procollagen mRNA levels at week 4. The topical agents used were Resveratrol (trans-3,5,4-trihydroxystilbene) 1%; Glycolic acid 8%; Retinaldehyde 0.05%; Madecassoside 1% and Retinoic acid 0.05%, along with no agent.

In the above paragraphs and FIGS. 11 to 43, the following legend is used: LLLT=Low Level Light Therapy; Light PRE=LLLT has been applied 15 min before the topical agent; Light POST=LLLT has been applied 15 min after the topical agent; 660P=Pulsed* LLLT @660 nm; 660 C=Continuous Wave LLLT @660 nm; 940P=Pulsed LLLT @940 nm; 940 C=Continuous Wave LLLT @940 nm. Pulsed=Sequencial pulsing with a duty cycle of 50% (D50), surface illuminated=1.5 cm$^2$ The test areas will be exposed to 660 nm or 940 nm wavelength delivered in either a sequential pulsing mode or a continuous (CW) mode, using a custom-built LED device based on LumiPhase™ technology. For the pulsing mode, the power density was of 10 mW/cm2 for 800 s. The pulsing patterns and time on-and-time-off sequences were as follows: Pulse duration (time on [PD]) 500 μsec, pulse interval (time off [PI]) 150 μsec, 4 pulses per pulse train (PPT), and a pulse train interval (PTI) of 1550 μsec. For the CW mode, an irradiance of 10 mW/cm2 was used for 400 sec.

PCR results are shown in FIGS. 11 to 38. Potential applications include dermatological indications where topical agents are used, including: anti-aging, acne treatments, PDT and Scar management.

Example 11: Photopreparation In-Vivo Using Pulsed Light and Comparison with CW It has been known for years that increasing tissue temperature will increase clinical efficacy of some topicals like photosensitizers. The heat source may be physical like a bean bag but may also be a light-based device. Apart from this temperature-dependent approach no other mechanism of action has been described. Photopreparation uses photobiomodulation principles to prepare the skin so as to enhance the efficacy of topicals.

In order to measure the effect of photopreparation on the skin we used an LED device (Lumiphase 940 nm, CW and Pulsed, irradiance: 70 mW/cm2, OpusMed, Montreal, Canada) prior to the application of a photosensitizer (5-ALA: Levulan, Kerastick, DUSA Pharmaceuticals, USA). We tested both CW and sequential pulsing modes 24 h and 30/15 minutes (total fluence 63 J/cm$^2$ before the application of 5-ALA for 3 hours). Following an incubation time of 3 hours, we measured the fluorescence induced by the conversion of 5-ALA to protoporphyrin IX (PpIX) with a dedicated device (Fluoderm, Dia-Medico ApS, Danemark). The pulsed radiation, referred to as D50 hereinbelow, consisted in pulse trains of 4 pulses with pulses lasting 500 μs separated with an inter-pulse interval within each train of 150 μs. The pulse trains were separated from each other by 1550 μs. The results are presented in the following table. Higher numbers mean higher conversion to PpIX, and thus indicate that the PDT treatment will be more efficient. All parameters were tested on adjacent portion of the subject's skin. The experiment was performed on the back of a 39 yr old male with phototype I.

| Conditions | Fluoderm Measurements | | | |
| --- | --- | --- | --- | --- |
| | Before PP (24 h pre-5-ALA) | Before PP (30 & 15 min pre-5-ALA) | Post 3 hour incubation (5-ALA) | Fold increase |
| PP 24 h pre-5-ALA: D50 - 30 min | 19 | 21 | 72 | 1.45 |
| PP 24 h pre-5-ALA: CW - 15 min | 20 | 21 | 56 | 1.13 |
| PP 30 min pre-5-ALA: D50 - 30 min | 20 | 22.5 | 59 | 1.19 |
| PP 15 min pre-5-ALA: CW - 15 min | 22.5 | 23.5 | 51 | 1.03 |
| Positive control: 5-ALA alone | 23.5 | 25 | 49.5 | 1 |
| Negative control: No 5-ALA | 24 | 25.5 | 24 | |

PP: Photopreparation

Using D50 sequentially pulsed photopreparation 24 h prior to the application of 5-ALA gave the best fluorescence score (2.1-fold increase compared to 5-ALA alone (control)). The second best score was obtained with D50 again when applied 30 min prior to the application of 5-ALA (1.45 fold-increase). CW photopreparation-induced fluorescence was less impressive but showed better results when used 24 h before compared to 15 min prior to the application of 5-ALA (1.43 vs 1.09-fold increase respectively).

Sequentially pulsed photopreparation is superior to CW mode to enhance PpIX-induced fluorescence. Moreover, the use of this device-based skin preparation is optimal when used at least 24 hours prior to the application of the topical.

The exact mechanism of action involved is non-thermal since the best results were obtained when photopreparation was performed 24 hours before the application of the topical and then undoubtedly related to photobiomodulation cell signaling pathways. Indeed, after 24 hours, any thermal effect would disappear as skin temperature would necessarily have returned to normal. Also, if thermal effects were a main cause of improved conversion, there would be no difference with the CW and D50 protocols. These results show a new surprising result that irradiation with LEDs in the infrared region of the spectrum prior to PDT with 5-ALA a long time before 5-ALA is applied on skin surprisingly increases conversion of 5-ALA.

In view of these promising results, another study with even longer delays before application of 5-ALA was performed. The back skin of two test subjects was irradiated with continuous wavelength and pulsed infrared light at 940 nm. These irradiations took place 50-53, 24-29, and 8-14 hours prior to the application of the 5-ALA. After a three-hour incubation period with the compound, a FluoDerm™ device was used to measure the fluorescence of the skin (Emitting wavelength: 400-420 nm; Measuring excitation wavelength: 610-720 nm nm) a direct indication of the activity of 5-ALA. 5-ALA must penetrate the skin and then be converted to PpIX before any fluorescence increase can be observed. Results: Several pulsed (as in protocol D50 referred to above) and some CW conditions at 940 nm—up to 53 hours' pre-irradiation—showed statistically significant increase in fluorescence (p=0.05) (Fluoderm™ readings) compared to the no-irradiation, 5-ALA only control. Conclusion: This preconditioning method uses a temperature-independent mechanism of action via cell signaling pathways as in photobiomodulation. In this study, pulsing was superior to CW mode.

Results and statistical analysis for each subject are as follows:

| Conditions DB | | Fluoderm Reading | t-test Statistic | Looked Up* P-Values (for the 2-tailed test here) | The result is significant at p < ... | |
|---|---|---|---|---|---|---|
| 50 hour time points | D50-940 | 35.0 | 3.139 | 0.020 | 0.05 | 0.10 |
| | CW-940 | 45.0 | −1.087 | 0.319 | ~ | ~ |
| 24 hour time points | D50-940 | 36.5 | 2.505 | 0.046 | 0.05 | 0.10 |
| | CW-940 | 48.0 | −2.354 | 0.057 | ~ | 0.10 |
| 14 hour time points | D50-940 | 44.5 | −0.875 | 0.415 | ~ | ~ |
| | CW-940 | 51.0 | −3.622 | 0.011 | 0.05 | 0.10 |
| Control | Just 5-ALA | 37.0 | 2.294 | 0.062 | ~ | 0.10 |

| Sample Number | Mean | Sample Standard Deviation |
|---|---|---|
| 7 | 42.4 | 6.261 |

| Conditions GC | | Fluoderm Reading | t-test Statistic | Looked Up* P-Values (for the 2-tailed test here) | The result is significant at p < ... | |
|---|---|---|---|---|---|---|
| 53 hour time points | D50-940 | 46.5 | 2.324 | 0.045 | 0.05 | 0.10 |
| | CW-940 | 55.0 | −4.732 | 0.001 | 0.05 | 0.10 |
| | S50-940 | 55.0 | −4.732 | 0.001 | 0.05 | 0.10 |
| 29 hour time points | D50-940 | 52.0 | −2.241 | 0.052 | ~ | 0.10 |
| | CW-940 | 47.0 | 1.909 | 0.089 | ~ | 0.10 |
| | S50-940 | 47.5 | 1.494 | 0.169 | ~ | ~ |
| 8 hour time points | D50-940 | 49.0 | 0.249 | 0.809 | ~ | ~ |
| | CW-940 | 44.0 | 4.400 | 0.002 | 0.05 | 0.10 |
| | S50-940 | 51.0 | −1.411 | 0.192 | ~ | ~ |
| Control | Just 5-ALA | 46.0 | 2.739 | 0.023 | 0.05 | 0.10 |

| Sample Number | Mean | Sample Standard Deviation |
|---|---|---|
| 10 | 49.3 | 3.809 |

N.B.:
*http://www.socscistatistics.com/pvalues/tdistribution.spx
~means that this particular Fluorderm reading is not significantly different from the mean of these values.

Figure 44:
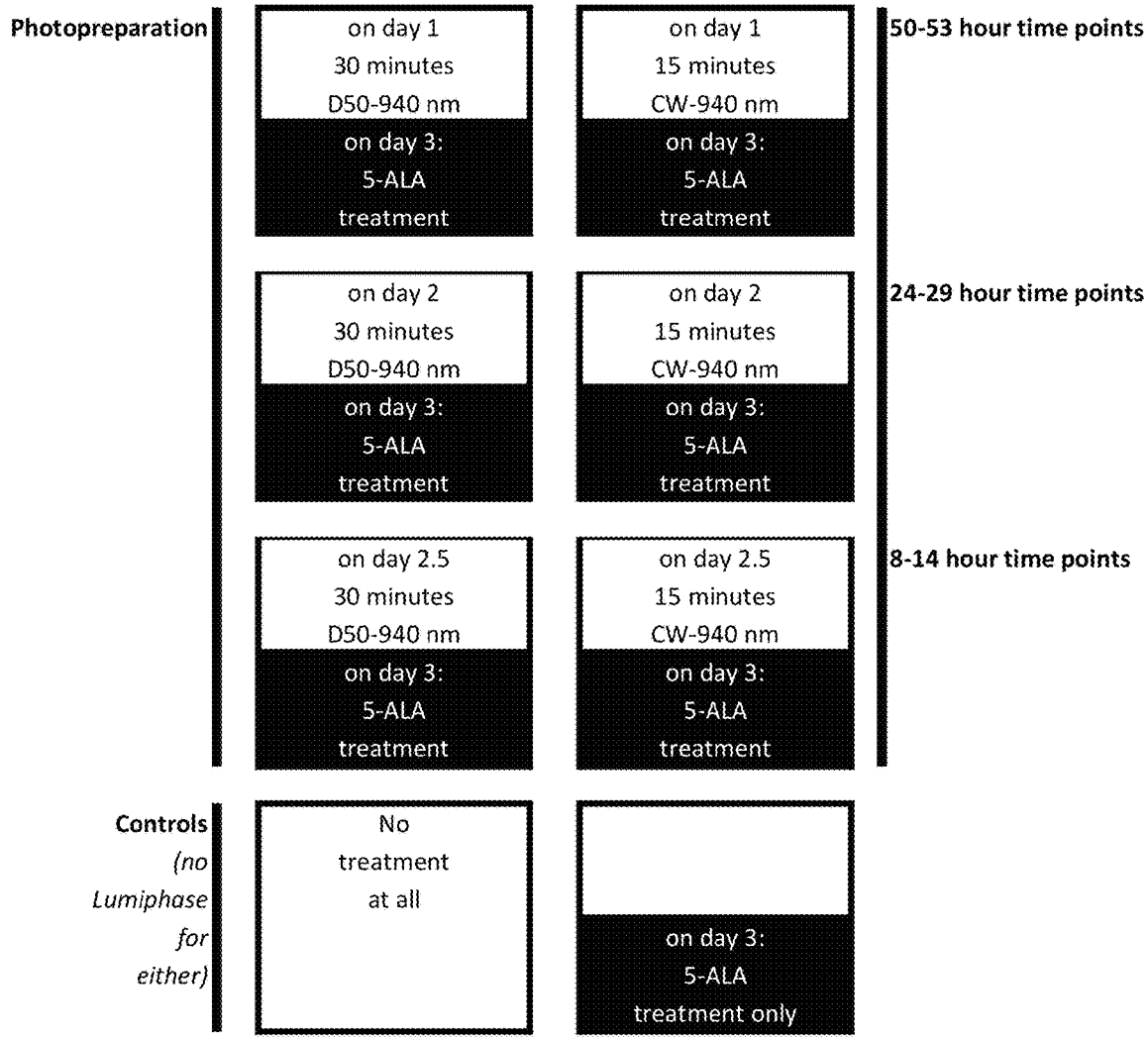
FIG. 44, in a schematic view, illustrates an experimental protocol for testing non-thermal effects of pre-ALA-5 application in PDT.

Example 12: Photopreparation In-Vivo Using Pulsed Light and Comparison with CW To obtain greater statistical power and investigate even longer term effects, the above study was repeated on other subjects. Below, the results or comparison between the D50 and CW protocols are shown for 4 subjects. Irradiation was performed in accordance with the pattern of FIG. 44, with measurements taken 24, 48 and 72 hours after pre-treatment with D50 and CW, instead of 8-14, 24-29 and 50-53.

More specifically, delineated treatment areas were drawn on each subject's back. These spaces had to be close enough together to enable simultaneous irradiation downstream in the experiment. Areas of each patient's back were then irradiated according to the predetermined photopreparation treatment parameter at the appropriate pre-5-ALA application and activation time. In this study, two light pulsing options were compared—pulsed versus continuous. Both options were set at 940 nm. The time set between the photopreparation treatment and the 5-ALA application was the other variable tested. Hence, for both pulsed and continuous modes, 72, 48 and 24 hour pre-treatments were performed on the appropriate back skin area. Following the appropriately timed photopreparation treatment of the correct back skin area, 20% 5-aminolevulinic acid (Levulan Kerastick, Dusa, Wilmington, USA) was applied to the patient's back. After the topical application, an incubation time of 3 hours was set to optimize the transformation of the medication to protoporphyrin IX (PpIX). Finally, using the Fluoroderm device, the fluorescence of each subject's back areas was measured. The recorded data was statistically analyzed.

Besides the 20% 5-aminolevulinic acid (Levulan Kerastick, Dusa, Wilmington, USA) used as the photosensitizer and the FluoDerm (Dia-Medico, Denmark) to quantify the fluorescence of each patient's back, a prototype able to irradiate the back skin areas with pulsed (D50 pulsing condition) and continuous wavelength (CW) light at 940 nm was built. This machine was assembled at RoseLab Skin Optics Research Laboratory (Montreal, Canada). The D50-940 nm condition was made up of 940 nm light with a pulsing pattern consisting of a 50% duty cycle delivered in the repeating pattern (in μseconds where PD, PI, and PTI mean pulse duration, pulse interval, and pulse train interval, respectively) of: PD 500 on, PI 150 off, PD 500 on, PI 150 off, PD 500 on and PTI 1550 off (FIG. 3). The irradiance delivered for all conditions (D50 and CW) was 75 mW/cm$^2$ and the fluence delivered for all conditions was 67.5 J/cm$^2$ (940 nm LED treatment duration D50=30 min and CW=15 min).

The FluoDerm measured each tested condition. These measurements were then compared to the control (only 5-ALA without photopreparation). The means of these proportional changes were calculated. The final results were categorized by every photopreparation condition (72, 48 and 24 hours pre-treatment). A 95% confidence interval was calculated for each mean.

The data is analyzed and presented as X-fold changes (or differences) as compared to the just 5-ALA control below. Higher number show a higher effect of pre-treatment with IR radiation.

|  |  | Mean | Standard Deviation | The 95% Confidence Interval Range | |
|---|---|---|---|---|---|
| 72 hours | D50-940 | 0.94 | 0.14 | 0.78 | 1.09 |
|  | CW-940 | 1.05 | 0.22 | 0.8 | 1.3 |
| 48 hours | D50-940 | 1.08 | 0.17 | 0.91 | 1.25 |
|  | CW-940 | 1.34 | 0.11 | 1.23 | 1.45 |
| 24 hours | D50-940 | 1.27 | 0.29 | 0.99 | 1.55 |
|  | CW-940 | 1.18 | 0.16 | 1.02 | 1.34 |

This table shows the very surprising result that pretreatment with the proposed IR illumination schemes has positive effect on 5-ALA treatment after 24 hours, and even after 48 hours. Therefore, pre-treatment with either D50 or CW, or other suitable IR irradiation protocols from about 12 hr to about 60 hr, for example from about 16 hr to about 60 hr or from about 24 hr to about 60 hr, or from about 24 hr to about 48 hr prior to 5-ALA PDT would be beneficial. Due to typical operating hours of clinics that perform 5-ALA PDT, such pretreatment could be performed for example from about 16 to about 32 hours prior to ALA treatment, or from about 40 to about 56 hours prior to ALA treatment, in other words, 1 or 2 days prior (24 or 48 hours+/−8 hours). In a very specific case, IR pre-treatment could be performed (24 or 48 hours+/−1 or 2 hours) prior to 5-ALA treatment.

Of note, one of the subject did not show any increase in fluorescence following NIR preconditioning pre-PDT. We found out that he had ingested alcohol (9 beers) the evening following the NIR exposure. This may explain the lack of response to NIR preconditioning. Alcohol augments the inducibility of delta-aminolevulinic acid synthase. Alcohol has many biochemical and clinical effects on porphyrin and heme synthesis both in humans and laboratory animals. Ethanol suppresses the activity of porphobilinogen synthase (synonym: delta-aminolevulinic acid dehydratase), uroporphyrinogen decarboxylase, coproporphyrinogen oxidase, and ferrochelatase, whereas it induces the first and rate-limiting enzyme in the pathway, delta-aminolevulinic acid synthase and also porphobilinogen deaminase. Alcohol intake is therefore a likely counter-indication to the proposed treatments.

It has been known for a long time that raising tissue temperature enhances the conversion of 5-ALA to PpIX during PDT. The application of an "outside-in" heat source like a bean bag or heating pad on the skin is enough to provide this effect, leading to better clinical results. What if a heat source would allow for superior, more uniform innovative "inside-out" pre-heating. Actually, NIR light can penetrate the deep dermis. It is absorbed by water which can raise the skin temperature up to 42° C. This method called photopreparation, when NIR is applied 15 minutes prior to 5-ALA application, has been shown to increase the conversion of 5-ALA to PpIX, ultimately improving PDT anti-acne effects [3]. Based on this photopreparation thermal method, we decided to extend the concept to search for a non-thermal preconditioning mechanism of action. By extending the delay between NIR irradiation of skin and the application of 5-ALA to several hours/days, the temperature increase would have time to dissipate allowing for the measurement of non-thermal preconditioning effects like in photoprevention.

REFERENCES

I. Cunliffe W J, Simpson N B. Disorders of the sebaceous glands. In Champion R H, Burton J L, Burns D A, Breathnach S M, eds. Textbook of Dermatology 6th edn, Vol. 3. Oxford: Blackwell Science. 1998: 1940-1973.

II. Bojar R A, Holland K T. Acne and *Propionibacterium acnes*. Clin Dermatol 2004; 22:375-379.

III. Ashkenazi H, Malik Z, Harth Y, Nitzan Y. Eradication of *Propionibacterium acnes* by its endogenous porphyrins after illumination with high intensity blue light. FEMS Immunol Med Microbiol 2003; 35:17-24.

IV. Borelli C, Merk K, Schaller M, Jacob K, Vogeser M, Weindl G, Berger U, Plewig G. In vivo Porphyrin Production by *P. acnes* in Untreated Acne Patients and its Modulation by Acne Treatment. Acta Derm Venereol 2006; 86:316-319.

V. Divaris D X, Kennedy J C, Pottier R H. Phototoxic damage to sebaceous glands and hair follicles of mice after systemic administration of 5-aminolevulinic acid correlates with localized protoporphyrin IX fluorescence. Am J Pathology 1990; 136:891-897.

VI. de Bruijn H S, Meijers C, van der Ploeg-van den Heuvel A, Sterenborg H J, Robinson D J. Microscopic localisation of protoporphyrin IX in normal mouse skin after topical application of 5-aminolevulinic acid or methyl 5-aminolevulinate. J Photochem Photobiol B 2008; 92:91-7.

VII. Gerscher S, Connelly J P, Beijersbergen Van Henegouwen G M, MacRobert A J, Watt P, Rhodes L E. A quantitative assessment of protoporphyrin IX metabolism and phototoxicity in human skin following dose-controlled delivery of the prodrugs 5-aminolaevulinic acid and 5-aminolaevulinic acid-n-pentylester. Br J Dermatol 2001; 144:983-990.

VIII. Hongcharu W, Taylor C R, Chang Y, Aghassi D, Suthamjariya K, Anderson R R. Topical ALA-photodynamic therapy for the treatment of acne vulgaris. J Invest Dermatol 2000; 115:183-192.

IX. Kawada A, Aragane Y, Kameyama H, Sangen Y, Tezuka T. Acne phototherapy with a high-intensity, enhanced, narrow-band, blue light source: an open study and in vitro investigation. J Dermatol Sci 2002; 30:129-135.

X. Divaris D X, Kennedy J C, Pottier R H. Phototoxic damage to sebaceous glands and hair follicles of mice after systemic administration of 5-aminolevulinic acid correlates with localized protoporphyrin IX fluorescence. Am J Pathol 1990; 136:891-897

XI. Haedersdal M, Togsverd-Bo K, Wulf H C. Evidence-based review of lasers, light sources and photodynamic therapy in the treatment of acne vulgaris. J Eur Acad Dermatol Venereol 2008; 22:267-278.

XII. Hamilton F L, Car J, Lyons C, Car M, Layton A, Majeed A. Laser and other light therapies for the treatment of acne vulgaris: systematic review. Br J Dermatol 2009; 160: 1273-1285.

XIII. Taylor M N, Gonzalez M L. The practicalities of photodynamic therapy in acne vulgaris. Br J Dermatol 2009; 160:1140-1148.

XIV. Hull W. Heat enhanced transdermal drug delivery: a survey paper. J Appl Res Clin Exp Ther 2002; 2:1-9.

XV. S. K. Chang and J. E. Riviere, Percutaneous absorption of parathion in vitro in porcine skin: effects of dose, temperature, humidity, and perfusate composition on absorptive flux, Fundam Appl Toxicol 1991; 17:494-504.
XVI. Clarys, K. Alewaeters, A. Jadoul, A. Barel, R. Oliviera Manadas and V. Preat, In vitro percutaneous penetration through hairless rat skin: influence of temperature, vehicle and penetration enhancers. Eur J Pharm Biopharm 1998; 46:279-283.
XVII. H. Durrheim, G. L. Flynn, W. I. Higuchi and C. R. Behl, Permeation of hairless mouse skin I: experimental methods and comparison with human epidermal permeation by alkanols, J Pharm Sci 1980; 69:781-786.
XVIII. Juzenas P, Sørensen R, Iani V, Moan J. Uptake of topically applied 5-aminolevulinic acid and production of protoporphyrin IX in normal mouse skin: dependence on skin temperature. Photochem Photobiol 1999; 69:478-481.
XIX. Moan J, Berg K, Gadmar O B, Iani V, Ma L, Juzenas P. The temperature dependence of protoporphyrin IX production in cells and tissues. Photochem Photobiol 1999; 70:669-673.
XX. Juzeniene A, Juzenas P, Kaalhus O, Iani V, Moan J. Temperature effect on accumulation of protoporphyrin IX after topical application of 5-aminolevulinic acid and its methylester and hexylester derivatives in normal mouse skin. Photochem Photobiol 2002; 76:452-456.
XXI. Juzeniene A, Juzenas P, Bronshtein I, Vorobey A, Moan J. The influence of temperature on photodynamic cell killing in vitro with 5-aminolevulinic acid. J Photochem Photobiol B 2006; 84:161-166.
XXII. van den Akker J T, Boot K, Vernon D I, Sterenborg H J, Brown S B. Effect of elevating the skin temperature during topical ALA application on in vitro ALA penetration through mouse skin and in vivo PpIX production in human skin. Photochem Photobiol Sci 2004; 3:263-267.
XXIII. Rud E, Gederaas O, Hegset A, Berg K. 5-aminolevulinic acid, but not 5-aminolevulinic acid esters, is transported into adenocarcinoma cells by system BETA transporters. Photochem Photobiol 2000; 71:640-647.
XXIV. Dover J S, Phillips T J, Arndt K A. Cutaneous effects and therapeutic uses of heat with emphasis on infrared radiation. J Am Acad Dermatol 1989; 20:278-286.
XXV. Barolet, D. Light-Emitting Diodes (LEDs) in Dermatology. Semin Cutan Med Surg 2008; 27:227-238
XXVI. Morton C A, McKenna K E, Rhodes L E; British Association of Dermatologists Therapy Guidelines and Audit Subcommittee and the British Photodermatology Group. Guidelines for topical photodynamic therapy: update. Br J Dermatol 2008; 159:1245-1266
XXVII. Tan J K L. Current Measures for the Evaluation of Acne Severity. Expert Rev Dermatol 2008; 3:595-603.
XXVIII. Fitzpatrick T B. The validity and practicality of sun-reactive skin types I through VI. Arch Dermatol 1988; 124:869-871.
XXIX. Schieke S M, Schroeder P, Krutmann J. Cutaneous effects of infrared radiation: from clinical observations to molecular response mechanisms. Photodermatol Photoimmunol Photomed 2003; 19:228-234
XXX. Keyvan N, Villafradez-Diaz L M. Light/laser therapy in the treatment of acne vulgaris. Journal of Cosmetic Dermatology 2005 4; 318-320
XXXI. Desmet K D, Paz D A, Corry J J, Eells J T, Wong-Riley M T, Henry M M, Buchmann E V, Connelly M P, Dovi J V, Liang H L, Henshel D S, Yeager R L, Millsap D S, Lim J, Gould L J, Das R, Jett M, Hodgson B D, Margolis D, Whelan H T. Clinical and experimental applications of NIR-LED photobiomodulation. Photomed Laser Surg 2006; 24:121-128.
XXXII. Whelan H T, Smits R L Jr, Buchman E V, Whelan N T, Turner S G, Margolis D A, Cevenini V, Stinson H, Ignatius R, Martin T, Cwiklinski J, Philippi A F, Graf W R, Hodgson B, Gould L, Kane M, Chen G, Caviness J. Effect of NASA light-emitting diode irradiation on wound healing. J Clin Laser Med Surg 2001; 19:305-314.
XXXIII. Barolet, D, Szeimies, R M, Adatto, M, Zelickson, B, Gold, M. Photodynamic Therapy: Will it hit its stride anytime soon?. Controversies and Conversations in Laser and Cosmetic Surgery. Skin and Aging 2007; December Supplement:7-10.
XXXIV. Gerritsen M J, Smits T, Kleinpenning M M, van de Kerkhof P C, van Erp P E. Pretreatment to enhance protoporphyrin IX accumulation in photodynamic therapy. Dermatology 2009; 218:193-202.
XXXV. Braathen L R, Szeimies R M, Basset-Seguin N, Bissonnette R, Foley P, Pariser D, Roelandts R, Wennberg A M, Morton C A; International Society for Photodynamic Therapy in Dermatology. Guidelines on the use of photodynamic therapy for nonmelanoma skin cancer: an international consensus. International Society for Photodynamic Therapy in Dermatology 2005. J Am Acad Dermatol 2007; 56:125-143.
XXXVI. Lehmann P. Methyl aminolaevulinate-photodynamic therapy: a review of clinical trials in the treatment of actinic keratoses and nonmelanoma skin cancer. Br J Dermatol 2007; 156: 793-801.

Although the present invention has been described hereinabove by way of preferred embodiments thereof, it can be modified, without departing from the spirit and nature of the subject invention as defined in the appended claims.

What is claimed is:

1. A method for treating skin tissues, said skin tissues defining an epidermal layer and a sub-epidermal layer, said epidermal layer defining a skin surface and said sub-epidermal layer extending from said epidermal layer substantially opposite to said skin surface, said method comprising:
    positioning a radiation source outside of said skin tissues at a predetermined distance from said skin surface, said radiation source including light emitting diodes;
    powering said light emitting diodes so as to produce infrared radiation having a predetermined spectrum and a predetermined power;
    irradiating a predetermined region of said sub-epidermal layer for a predetermined duration of from 1 minute to 1 hour with said infrared radiation through said epidermal layer, said predetermined spectrum and said predetermined power being such that said infrared radiation is absorbed to a larger degree in said sub-epidermal layer than in said epidermal layer;
    waiting for a predetermined delay after irradiating said predetermined region for said predetermined duration, wherein the predetermined delay is between 24 and 72 hours; and
    applying a treatment substance on said skin surface immediately after said predetermined delay.

2. A method as defined in claim 1 wherein said treatment substance includes a photo-activatable substance, said method further comprising irradiating said skin tissues with radiation having a spectrum and a power density suitable for activating said photo-activatable substance.

3. A method as defined in claim 2, wherein said treatment substance is selected from the group consisting of porphyrin, chlorine, 5-ALA, xanthene and phtalocyanine derivatives.

4. A method as defined in claim 3, wherein said skin tissues include skin tissues having a condition selected from the set consisting of actinic karatosis, acne, inflammatory acne and diffuse sebaceous glands hyperplasia.

5. A method as defined in claim 1, wherein said infrared radiation includes pulses of a pulse duration separated by an inter-pulse interval.

6. A method as defined in claim 5, wherein said pulse duration is from about 100 microseconds to about 5 milliseconds.

7. A method as defined in claim 5, wherein said pulse duration is from about 250 microseconds to about 1 millisecond.

8. A method as defined in claim 5, wherein said inter-pulse interval is from about 50 microseconds to about 0.5 millisecond.

9. A method as defined in claim 5, wherein the pulses are grouped in pulse trains, all pulses within a pulse train having the same pulse duration and being separated from each other by the same inter-pulse interval, the pulse trains being separated from each other by an inter-pulse train interval larger than the inter-pulse interval.

10. The method as defined in claim 9, wherein the inter-pulse train interval is from about 500 microsecond to about 1 second.

11. The method as defined in claim 9, wherein the inter-pulse train interval is from about 750 microseconds to about 500 milliseconds.

12. The method as defined in claim 9, wherein the inter-pulse train interval is from about 500 microseconds to about 2.25 milliseconds.

13. The method as defined in claim 9, wherein a number of pulses within each pulse train is from 2 to 1000 pulses.

14. The method as defined in claim 9, wherein a number of pulses within each pulse train is from 3 to 10 pulses.

15. A method as defined in claim 1, wherein said predetermined spectrum includes wavelengths contained within an interval of from about 800 nm to about 1000 nm.

16. A method as defined in claim 1, wherein said predetermined spectrum includes a peak at one of about 940 nm, about 870 nm, and about 970 nm, said peak having a bandwidth of less than about 30 nm.

17. A method as defined in claim 1, further comprising:
measuring a skin temperature of said skin tissues while irradiating said sub-epidermal layer with said infrared radiation; and
stopping irradiation of said sub-epidermal layer when said skin temperature reaches a predetermined temperature.

18. The method as defined in claim 17, wherein said predetermined temperature is about 38° C.

19. The method as defined in claim 17, wherein said predetermined temperature is about 41° C.

20. A method as defined in claim 1, wherein said sub-epidermal layer is irradiated with a fluence of from about 50 J/cm$^2$ to about 300 J/cm$^2$.

21. A method as defined in claim 1, wherein said infrared radiation is pulsed with duty cycle of between 15% and 85%.

22. A method as defined in claim 21, wherein said infrared radiation has a duty cycle of about 50%.

23. A method as defined in claim 1, wherein said infrared radiation has a power of from about 1 mW/cm$^2$ to about 1 W/cm$^2$.

24. A method as defined in claim 1, wherein said infrared radiation has a power of from about 30 mW/cm$^2$ to about 250 mW/cm$^2$.

25. A method as defined in claim 1, wherein said infrared radiation has a power of from about 20 mW/cm$^2$ to about 100 mW/cm$^2$.

26. The method as defined in claim 1, wherein the infrared radiation is continuous wave radiation.

27. A method as defined in claim 1, wherein said method is performed in vivo on a human subject.

28. A method for treating skin tissues, said skin tissues defining an epidermal layer and a sub-epidermal layer, said epidermal layer defining a skin surface and said sub-epidermal layer extending from said epidermal layer substantially opposite to said skin surface, said method comprising:
positioning a radiation source outside of said skin tissues at a predetermined distance from said skin surface, said radiation source including light emitting diodes;
powering said light emitting diodes so as to produce infrared radiation having a predetermined spectrum and a predetermined power;
irradiating a predetermined region of said sub-epidermal layer for a predetermined duration of from 1 minute to 1 hour with said infrared radiation through said epidermal layer, said predetermined spectrum and said predetermined power being such that said infrared radiation is absorbed to a larger degree in said sub-epidermal layer than in said epidermal layer;
waiting for a predetermined delay after irradiating said predetermined region for said predetermined duration, wherein the predetermined delay is between 16 and 72 hours;
applying a treatment substance on said skin surface immediately after said predetermined delay, wherein said treatment substance includes a photo-activatable substance; and
irradiating said skin tissues with radiation having a spectrum and a power density suitable for activating said photo-activatable substance.

29. The method as defined in claim 28, wherein said treatment substance is selected from the group consisting of porphyrin, chlorine, 5-ALA, xanthene and phtalocyanine derivatives.

30. The method as defined in claim 29, wherein said skin tissues include skin tissues having a condition selected from the set consisting of actinic karatosis, acne, inflammatory acne and diffuse sebaceous glands hyperplasia.

31. The method as defined in claim 28, wherein said predetermined spectrum includes wavelengths contained within an interval of from about 800 nm to about 1000 nm and said infrared radiation has a power of from about 30 mW/cm$^2$ to about 250 mW/cm$^2$.

* * * * *